(12) United States Patent
Kim

(10) Patent No.: US 9,545,212 B2
(45) Date of Patent: Jan. 17, 2017

(54) RECONFIGURABLE MEASURING APPARATUS AND METHOD FOR CONTROLLING APPARATUS

(71) Applicant: SAMSUNG ELECTRONICS CO., LTD., Suwon-si (KR)

(72) Inventor: Jong Pal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 156 days.

(21) Appl. No.: 14/199,319

(22) Filed: Mar. 6, 2014

(65) Prior Publication Data

US 2015/0065908 A1    Mar. 5, 2015

(30) Foreign Application Priority Data

Aug. 28, 2013 (KR) .................. 10-2013-0102309

(51) Int. Cl.

| | |
|---|---|
| *A61B 5/0408* | (2006.01) |
| *A61B 5/0478* | (2006.01) |
| *A61B 5/0492* | (2006.01) |
| *A61B 5/053* | (2006.01) |
| *H03F 3/387* | (2006.01) |
| *H03F 3/45* | (2006.01) |

(52) U.S. Cl.
CPC .......... *A61B 5/0408* (2013.01); *A61B 5/0478* (2013.01); *A61B 5/0492* (2013.01); *A61B 5/053* (2013.01); *H03F 3/387* (2013.01); *H03F 3/45995* (2013.01); *H03F 2200/271* (2013.01)

(58) Field of Classification Search
CPC . A61B 5/04004; A61B 5/0402; A61B 5/0428; A61B 5/04288; A61B 5/053; A61B 5/0531; A61B 5/7203; A61B 5/7225; A61B 5/7228; H03F 3/38–3/387; H03F 3/45995; H03F 1/26; H03F 2200/372

See application file for complete search history.

(56) References Cited

U.S. PATENT DOCUMENTS

| | | | |
|---|---|---|---|
| 7,391,257 B1 * | 6/2008 | Denison | A61B 5/0002 330/10 |
| 2003/0006782 A1 | 1/2003 | Shambroom et al. | |

(Continued)

FOREIGN PATENT DOCUMENTS

| | | |
|---|---|---|
| JP | 2011-19156 A | 1/2011 |
| KR | 10-2005-0097208 A | 10/2005 |
| KR | 10-2008-0088727 A | 10/2008 |
| KR | 10-2011-0019774 A | 2/2011 |

OTHER PUBLICATIONS

Extended European Search Report mailed Feb. 16, 2015 in European Application No. 14164826.1 (5 pages, in English).

(Continued)

*Primary Examiner* — Devin Henson
*Assistant Examiner* — Audrey J Parker
(74) *Attorney, Agent, or Firm* — NSIP Law

(57) ABSTRACT

A reconfigurable measuring apparatus includes a first chopper configured to modulate an input signal, and an amplifier configured to amplify an output signal of the first chopper. The reconfigurable measuring apparatus further includes a second chopper configured to demodulate an output signal of the amplifier, and a controller configured to control the first chopper and the second chopper based on a measurement mode.

28 Claims, 13 Drawing Sheets

(56) References Cited

U.S. PATENT DOCUMENTS

| | | |
|---|---|---|
| 2007/0043303 A1 | 2/2007 | Osypka et al. |
| 2010/0004517 A1 | 1/2010 | Bryenton et al. |
| 2011/0066054 A1* | 3/2011 | Yazicioglu ............... A61B 5/04 600/509 |
| 2011/0092834 A1* | 4/2011 | Yazicioglu ........... A61B 5/0402 600/509 |

OTHER PUBLICATIONS

Denison, Timothy, et al. "A 2.2 μW 94nV/√Hz, Chopper-Stabilized Instrumentation Amplifier for EEG Detection in Chronic Implants." Solid-State Circuits Conference, 2007. ISSCC 2007. Digest of Technical Papers. IEEE International. IEEE, 2007. (3 pages in English).

Ma, Chon-Teng, et al. "A 90nm CMOS bio-potential signal readout front-end with improved powerline interference rejection." Circuits and Systems, 2009. ISCAS 2009. IEEE International Symposium on. IEEE, 2009. (4 pages in English).

Manickam, Arun, et al. "Front-end integrated circuits for high-performance biological and chemical sensing." Circuits and Systems (MWSCAS), 2011 IEEE 54th International Midwest Symposium on. IEEE, 2011. (4 pages in English).

Xu, Jiawei, et al. "A 160 μW 8-channel active electrode system for EEG monitoring." Solid-State Circuits Conference Digest of Technical Papers (ISSCC), 2011 IEEE International. IEEE, 2011. (3 pages in English).

* cited by examiner

500

RECONFIGURABLE MEASURING APPARATUS AND METHOD FOR CONTROLLING APPARATUS

CROSS-REFERENCE TO RELATED APPLICATION

This application claims the benefit under 35 USC §119(a) of Korean Patent Application No. 10-2013-0102309, filed on Aug. 28, 2013, in the Korean Intellectual Property Office, the entire disclosure of which is incorporated herein by reference for all purposes.

BACKGROUND

1. Field

The following description relates to a reconfigurable measuring apparatus and a method for controlling the apparatus.

2. Description of Related Art

Various medical devices for examining a physical condition of a patient are being developed. The significance of medical devices for measuring electrical biosignals of a patient is being emphasized in terms of patient convenience during a health examination, quick provision of health examination results, and the like.

A biopotential may occur due to an electric field formed in a body, and be measured using a voltage of a predetermined part depending on a magnitude of the electric field. The origin of the biopotential is an excitable cell, which shows an electric excitation in response to an electric stimulus. The excitable cell may produce an action potential due to the electric excitation, and the action potential produced by the excitable cell may be transferred through a nerve fiber. By such an action potential, the electric field may be formed in a body.

Similar to a biopotential signal, an impedance signal may also be used for monitoring a physical condition or an emotional condition of a biological object.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a reconfigurable measuring apparatus including a first chopper configured to modulate an input signal, and an amplifier configured to amplify an output signal of the first chopper. The reconfigurable measuring apparatus further includes a second chopper configured to demodulate an output signal of the amplifier, and a controller configured to control the first chopper and the second chopper based on a measurement mode.

The measurement mode may include a biopotential measurement mode and an impedance measurement mode.

The controller may be configured to provide a frequency signal corresponding to a biopotential measurement mode to the first chopper and the second chopper in response to the measurement mode being the biopotential measurement mode.

The controller may be configured to control the first chopper for the input signal to bypass the first chopper in response to the measurement mode being an impedance measurement mode.

The controller may be configured to provide a frequency signal corresponding to an impedance measurement mode to the second chopper in response to the measurement mode being the impedance measurement mode.

The controller may be configured to provide a frequency signal corresponding to a biopotential measurement mode to the first chopper and the second chopper in response to the measurement mode being an impedance measurement mode and a carrier frequency for impedance measurement being within a band of noise caused by the amplifier.

The apparatus may further include an analog-to-digital converter (ADC) configured to perform an analog-to-digital conversion on an output signal of the second chopper, and a demodulator configured to demodulate the converted digital signal based on the carrier frequency.

The apparatus may further include a third chopper configured to demodulate an output signal of the second chopper, using the carrier frequency.

The controller may be configured to control the third chopper for the output signal of the second chopper to bypass the third chopper in response to the measurement mode being a biopotential measurement mode.

The controller may include a first multiplexer (MUX) configured to selectively provide a first frequency signal or a constant voltage signal to the first chopper, and a second MUX configured to selectively provide the first frequency signal or a second frequency signal to the second chopper.

The controller may further include a phase shifter configured to shift a phase of the second frequency signal.

The apparatus may further include a current generator configured to generate a current for impedance measurement based on the second frequency signal. The controller may be configured to activate the current generator in response to the measurement mode being an impedance measurement mode.

The apparatus may further include a first resistance unit configured to implement a resistance component between a node for a bias voltage and a node between the first chopper and the amplifier, using a capacitor and at least two switches. The controller may be configured to activate the first resistance unit in response to the measurement mode being a biopotential measurement mode.

The apparatus may further include a second resistance unit configured to implement a first resistance component between a node for a bias voltage and a first node between the first chopper and the amplifier, using at least two resistors, and implement a second resistance component having a same resistance value as the first resistance component between the node for the bias voltage and a second node between the first chopper and the amplifier, using the at least two resistors. The controller may be configured to activate the second resistance unit in response to the measurement mode being an impedance measurement mode.

The apparatus may further include a recovery unit configured to provide a voltage corresponding to a normal operation range of the amplifier to the amplifier.

In still another general aspect, there is provided a reconfigurable measuring apparatus including measuring modules, each of which is configured to measure a biopotential or an impedance, and a controller configured to control each of the measuring modules to measure a biopotential or an impedance. Each of the measuring modules includes a modulator configured to modulate an input signal, an amplifier configured to amplify an output signal of the modulator, and a demodulator configured to demodulate an output signal of the amplifier.

The controller may be configured to provide a first frequency signal to the modulator and the demodulator included in each of the measuring modules configured to measure a biopotential.

The first frequency signal may have a frequency higher than a band of noise caused by the amplifier included in each of the measuring modules configured to measure a biopotential.

The controller may be configured to provide a constant voltage signal to the modulator included in each of the measuring modules configured to measure an impedance, and provide a second frequency signal to the demodulator included in each of the measuring modules configured to measure an impedance.

The modulator included in each of the measuring modules configured to measure an impedance may be configured to have an input signal bypass the modulator.

The second frequency signal may have a frequency identical to a carrier frequency for impedance measurement.

In response to a carrier frequency for impedance measurement being within a band of noise caused by the amplifier included in each of the measuring modules configured to measure an impedance, the controller may be configured to provide a first frequency signal having a frequency higher than the band of noise to the modulator and the demodulator included in each of the measuring modules configured to measure an impedance.

In still another general aspect, there is provided a method of controlling a reconfigurable measuring apparatus, the method including receiving a signal indicating a measurement mode, providing a first signal to a first chopper based on the measurement mode, and providing a second signal to a second chopper based on the measurement mode. The first chopper may be configured to modulate an input signal, using the first signal, and the second chopper is configured to demodulate the modulated input signal amplified by an amplifier, using the second signal.

Each of the first signal and the second signal may include a frequency signal corresponding to a biopotential measurement mode in response to the measurement mode being the biopotential measurement mode.

The first signal may include a constant voltage signal, and the first chopper may be configured have the input signal bypass the first chopper, in response to the measurement mode being an impedance measurement mode.

The second signal may include a frequency signal corresponding to an impedance measurement mode in response to the measurement mode being an impedance measurement mode.

Each of the first signal and the second signal may include a frequency signal corresponding to a biopotential measurement mode in response to the measurement mode being an impedance measurement mode and a carrier frequency for impedance measurement being within a band of noise caused by the amplifier.

A non-transitory computer-readable storage medium may store a program comprising instructions to cause a computer to perform the method.

In yet another general aspect, there is provided a reconfigurable measuring apparatus including a first chopper configured to modulate a signal, and an amplifier configured to amplify the modulated signal. The reconfigurable measuring apparatus further includes a second chopper configured to demodulate the amplified signal, and a controller configured to control the first chopper and the second chopper based on whether a biopotential or an impedance of the signal is being measured.

The controller may be configured to provide a first frequency signal of a first frequency to the first chopper and the second chopper in response to the biopotential being measured, provide a constant voltage signal to the first chopper, and provide a second frequency signal of a second frequency greater than the first frequency to the second chopper, in response to the impedance being measured and the second frequency being outside a band of noise caused by the amplifier, and provide the first frequency signal to the first chopper and the second chopper in response to the impedance being measured and the second frequency being within the band of noise.

Other features and aspects will be apparent from the following detailed description, the drawings, and the claims.

Figure 1:
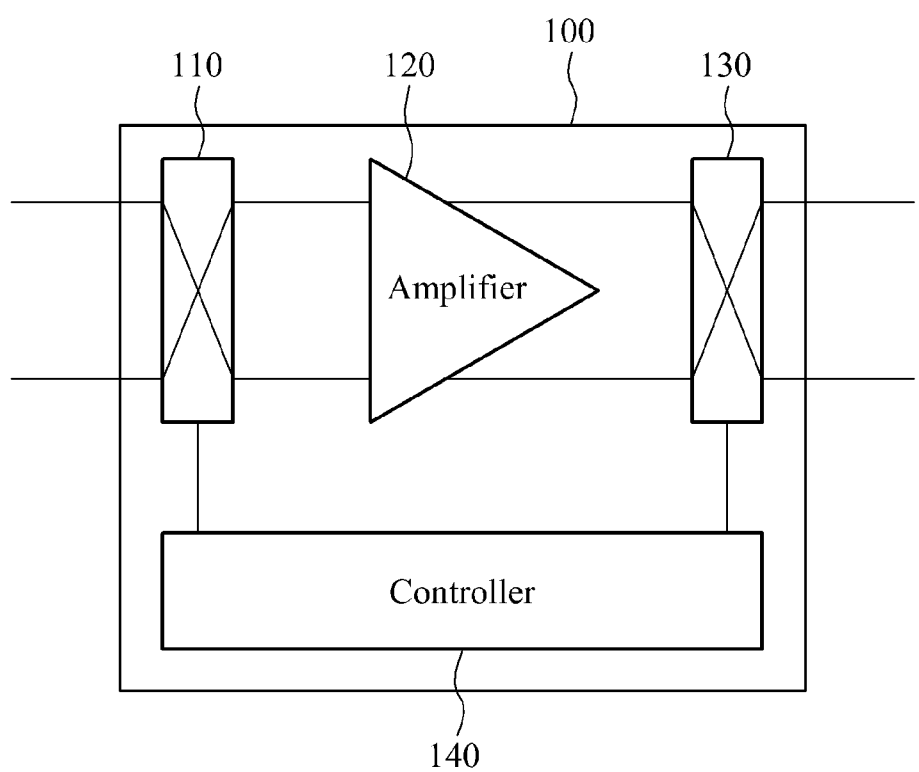
FIG. 1 is a block diagram illustrating an example of a reconfigurable measuring apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 illustrates an example of a reconfigurable measuring apparatus 100. Referring to FIG. 1, the reconfigurable measuring apparatus 100, hereinafter referred to as the "measuring apparatus", includes an amplifier 120, a plurality of choppers 110 and 130, and a controller 140.

The measuring apparatus 100 controls the first chopper 110 and the second chopper 130, using the controller 140, thereby being operable in various measurement modes. For example, the measuring apparatus 100 may measure a biopotential.

The biopotential may occur due to an electric field formed in a body, and be measured using a voltage of a predetermined part of the body, depending on a magnitude of the electric field. The biopotential may include an electrocardiogram (ECG), an electromyogram (EMG), an electroneurogram (ENG), an electroencephalogram (EEG), an electroretinogram (ERG), an electrooculogram (EOG), and/or other measurements known to one of ordinary skill in the art. An ECG measurement is performed to measure an electrical activity of a heart, using electrodes installed on a body surface. An EMG measurement is performed to measure a muscle contraction, using electrodes installed in a muscle. An ENG measurement is performed to measure a biopotential signal after a stimulus is provided, using electrodes installed in a peripheral nerve. For example, a nerve conduction velocity and a delay time may be measured through the ENG measurement. An EEG measurement is performed to measure an electrical activity of a brain, using surface electrodes installed around a head. An ERG measurement is performed to measure a visual response, using electrodes installed on a retina or an internal side surface of a retina. An EOG measurement is performed to measure an eye movement, using surface electrodes installed around an eye.

The controller 140 may control the first chopper 110 and the second chopper 130 to measure the biopotential. In order to measure the biopotential, the amplifier 120 may amplify a signal input through an electrode. The amplifier 120 may be a differential amplifier. The differential amplifier refers to an amplifier configured to amplify a difference between two input signals, and may include, for example, an instrumentation amplifier (IA).

In this example, noise may occur in the amplifier 120. For example, the noise occurring in the amplifier 120 may be 1/f noise. The 1/f noise is also referred to as flicker noise, and may be unique noise occurring in an active device. When the noise occurring in the active device is expressed on a frequency axis, a level of the noise may increase greatly in a low-frequency band, for example, less than or equal to 100 hertz (Hz). The level of the 1/f noise may increase in inverse proportion to a frequency.

Since the biopotential signal is a low-frequency signal, the noise occurring in the amplifier 120 may interfere with the biopotential signal. In order to prevent such interference, the controller 140 may control the first chopper 110 to modulate an input signal. For example, the controller 140 may control the first chopper 110 to modulate the input signal to a signal having a center frequency higher than a noise band. Accordingly, the amplifier 120 may amplify the modulated signal. Since the modulated signal has the center frequency beyond the noise band, the signal amplified by the amplifier 120 may not be affected by noise. In addition, the controller 140 may control the second chopper 130 to demodulate the amplified signal. For example, the controller 140 may control the second chopper 130 to demodulate the amplified signal to a signal having an original center frequency.

The measuring apparatus 100 may also measure impedance. Similar to the biopotential signal, an impedance signal may also be used to monitor a physical condition or an emotional condition of a biological object. For example, impedance indicating a degree of resistance of a skin, impedance indicating a degree of hydration of a skin, impedance that is changed based on pulmonary respiration, impedance that is changed based on a flow of a bloodstream, impedance existing on an electrical path including a measuring electrode, and/or other impedances known to one of ordinary skill in the art, may be measured.

The controller 140 may control the first chopper 110 and the second chopper 130 to be operated in an impedance measurement mode. In contrast to a biopotential measurement performed to measure a biopotential occurring in a body, impedance measurement may be performed using a current occurring outside the body. For example, when a current generated by a current generator is provided to a part of the body at which impedance is to be measured, the impedance of the part may cause a voltage drop. The measuring apparatus 100 may measure a potential difference resulting from the voltage drop, thereby measuring impedance.

A bioelectrical impedance analysis (BIA) may be based on a principle that a uniform conductor having an identical cross-sectional area of a predetermined length has a resistance proportional to the length and inversely proportional to the cross-sectional area. However, a human body is not in a shape of a uniform cylinder, and thus, a body conductance is not uniform. The human body includes muscles and extracellular fluids that conduct electricity relatively favorably, and adipose tissues that conduct electricity relatively unfavorably. Accordingly, various circuit models may be used to describe electrical characteristics of a body. For example, when an alternating current (AC) flows into a body, the current may pass through a cell membrane, and the cell membrane may be charged with an electric charge. In this example, the cell membrane may act as a capacitor, and the electrical characteristics of the body may be modeled using the cell membrane acting as a capacitor. In addition, an electric permeability may vary for each frequency of the AC. For example, a 5 kilohertz (kHz) AC does not pass through a cell membrane, and thus, may be used for measurement of extracellular fluids. An AC of at least 100 kHz passes through a cell membrane, and thus, may be used for measurement of total body water (TBW).

When impedance is measured using an AC, a signal input into the measuring apparatus 100 may have a frequency of the AC as a center frequency. The input signal may be used similar to a signal modulated using the frequency of the AC. The input signal may be amplified by the amplifier 120 for measurement.

As described above, noise may occur in the amplifier 120. For example, 1/f noise may occur in the amplifier 120. Since the input signal has the frequency of the AC as the center frequency, the input signal may be free from interference of the noise occurring in the amplifier 120 when the center frequency of the input signal is out of a band of the noise occurring in the amplifier 120. The controller 140 may control the first chopper 110 for the input signal to bypass the first chopper 110. For example, the controller 140 may provide a constant voltage signal of operating voltage ($V_{dd}$) or a ground voltage (GND) to the first chopper 110.

The amplifier 120 may amplify the bypassed signal. Since the bypassed signal has a center frequency out of the noise band, the signal amplified by the amplifier 120 may not be affected by noise. In addition, the controller 140 may control the second chopper 130 to demodulate the amplified signal. Since the amplified signal has the frequency of the AC used for impedance measurement as a center frequency, the controller 140 may control the second chopper 130 to demodulate the amplified signal, using the corresponding center frequency.

The measuring apparatus 100 according to an example may be reconfigured in various measurement modes, depending on an application. In addition, as to be described hereinafter, the measuring apparatus 100 according to an example may include a plurality of reconfigurable measuring modules. In this example, depending on an application, at least a portion of the measuring modules may be operated in a biopotential measurement mode, and a remaining portion of the measuring modules may be operated in an impedance measurement mode.

For example, an ECG may be measured using multiple channels since a form of an electric signal of a heart may be changed based on a direction at an outer part surrounding the heart. In this example, the measuring apparatus 100 may be reconfigured to measure the ECG, using multiple channels, and measure interface impedance between a skin and an input end of a measurement circuit for ECG measurement. When the ECG is measured using three channels, three measuring modules included in the measuring apparatus 100 may be reconstructed to be operated in a biopotential measurement mode. In addition, in order to measure the interface impedance at each channel, other three measuring modules included in the measuring apparatus 100 may be reconfigured to be operated in an impedance measurement mode. Further, since a real number component and an imaginary number component of an impedance signal may be measured based on a phase of a frequency provided to the second chopper 130, when measuring the impedance, still other three measuring modules included in the measuring apparatus 100 may be reconfigured to be operated in the impedance measurement mode.

Depending on an application, an impedance measurement may be unnecessary, or a biopotential measurement using more channels may be needed. The measuring apparatus 100 according to an example may provide technology that freely changes a configuration of the biopotential measurement and the impedance measurement, depending on the application.

Figure 2:
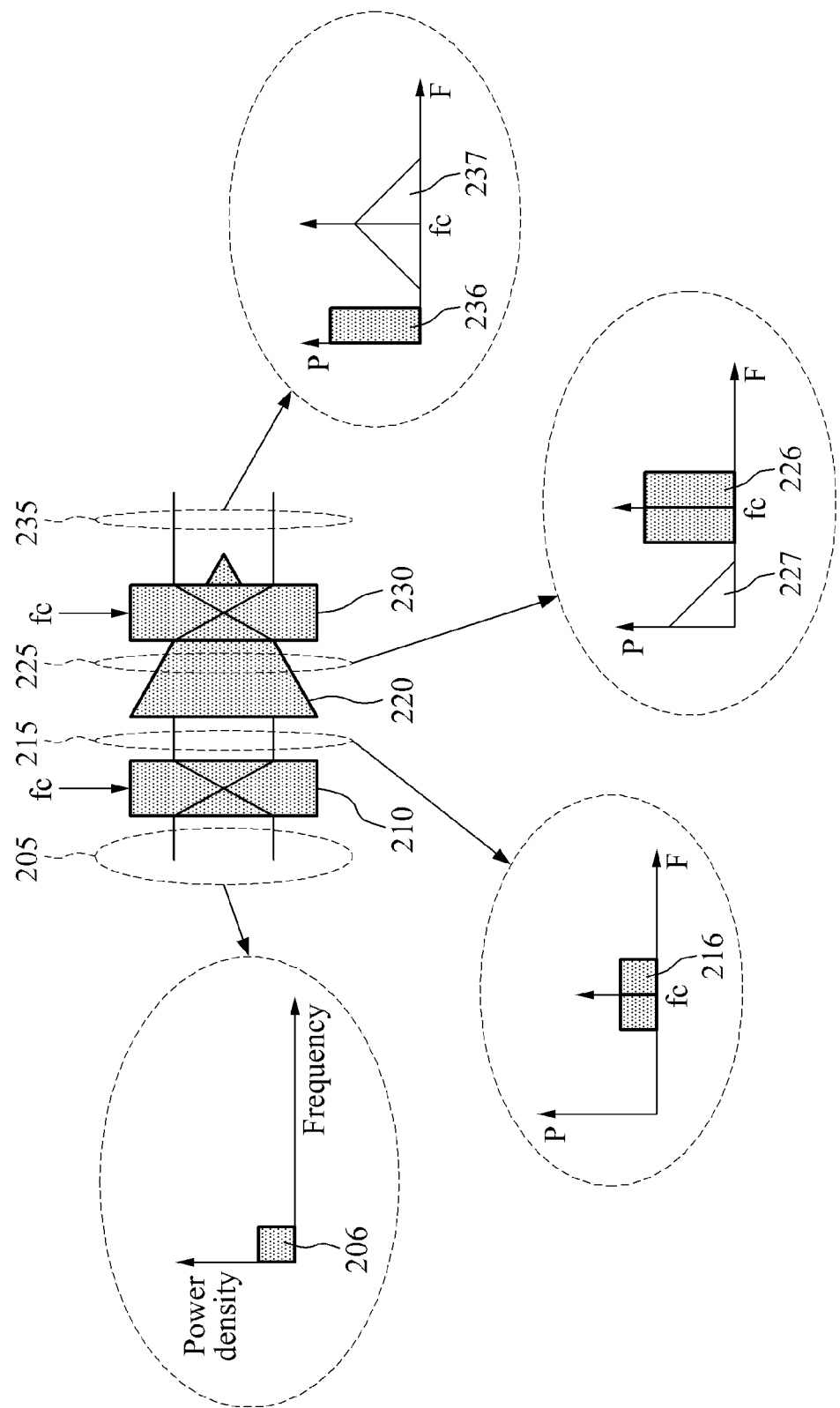
FIG. 2 is a diagram illustrating an example of an operation of a measuring apparatus that measures a biopotential signal.

FIG. 2 illustrates an example of an operation of a measuring apparatus 200 that measures a biopotential signal. Referring to FIG. 2, the measuring apparatus 200 includes a first chopper 210, an amplifier 220, and a second chopper 230. Although not shown in FIG. 2, the measuring apparatus 200 further includes a controller configured to control the first chopper 210 and the second chopper 230.

Hereinafter, modulation, amplification, and demodulation of an input signal passing the first chopper 210, the amplifier 220, and the second chopper 230 in a biopotential measurement mode will be described in detail. In each graph shown in FIG. 2, an x-axis denotes a frequency, and a y-axis denotes a power density. For example, a center frequency of an electric signal increases as a value of the x-axis increases, and an intensity of the electric signal increases as a value of the y-axis increases.

The measuring apparatus 200 receives the input signal for biopotential measurement, through an input end 205. Hereinafter, the input signal for biopotential measurement will be referred to as a biopotential signal. Since the biopotential signal is a direct current (DC) signal or a low-frequency signal, the biopotential signal may be expressed similar to a signal 206 in a graph corresponding to the input end 205. The biopotential signal occurring in a human body has a relatively low power density. Accordingly, the biopotential signal is amplified by the amplifier 220 in order to measure the biopotential signal. However, the amplifier 220 is an active device, and thus, 1/f noise occurs in the amplifier 220. The biopotential signal may be positioned within a band of the 1/f noise in a frequency domain. Accordingly, the 1/f noise may result in interference when the intact biopotential signal is amplified.

In order to prevent the interference, the controller provides a signal having a frequency fc higher than the band of the 1/f noise, to the first chopper 210. In this example, the biopotential signal may be expressed similar to a signal 216 in a graph corresponding to a node 215 between the first chopper 210 and the amplifier 220. The biopotential signal passes through the first chopper 210 to be modulated to the signal 216 having the frequency fc as a center frequency.

The signal 216 having the frequency fc as the center frequency is amplified by the amplifier 220. The biopotential signal may be expressed similar to a signal 226 in a graph corresponding to an internal portion 225 of the amplifier 220. The power density of the biopotential signal increases when the biopotential signal passes through the amplifier 220. In addition, the 1/f noise may be expressed similar to a signal 227 in the graph corresponding to the internal portion 225 of the amplifier 220. The 1/f noise occurs in a low-frequency band. The signal 226 and the signal 227 may not overlap in the graph corresponding to the internal portion 225 of the amplifier 220, which means that the biopotential signal may be free from interference of the 1/f noise, since the biopotential signal is modulated by the first chopper 210 to have the frequency fc as the center frequency.

The controller controls the second chopper 230 to demodulate the amplified signal 226. In detail, the controller provides a signal having the frequency fc to the second chopper 230. In this example, the biopotential signal may be expressed similar to a signal 236 in a graph corresponding to an output end 235. The biopotential signal passes through the second chopper 230 to be demodulated to the signal 236 having an original center frequency. At the same time, a signal corresponding to the 1/f noise passes through the second chopper 230 to be modulated to a signal 237 having the frequency fc as a center frequency. The signal 236 and the signal 237 may not overlap in the graph corresponding to the output end 235, which means that the biopotential signal may be free from the interference of the 1/f noise, since the biopotential signal is demodulated by the second chopper 230 and simultaneously, the 1/f noise is modulated by the second chopper 230.

The center frequency of the signal 236 in the graph corresponding to the output end 235 may be identical to the center frequency of the signal 206 in the graph corresponding to the input end 205, and the power density of the signal 236 in the graph corresponding to the output end 235 may be greater than the power density of the signal 206 in the graph corresponding to the input end 205, which means that the biopotential signal may be free from the interference of the 1/f noise although it is amplified and demodulated. As described above, the measuring apparatus 200 may provide technology that controls the first chopper 210 and the second chopper 230 for the biopotential signal to be amplified without being affected by the 1/f noise.

Figure 3:
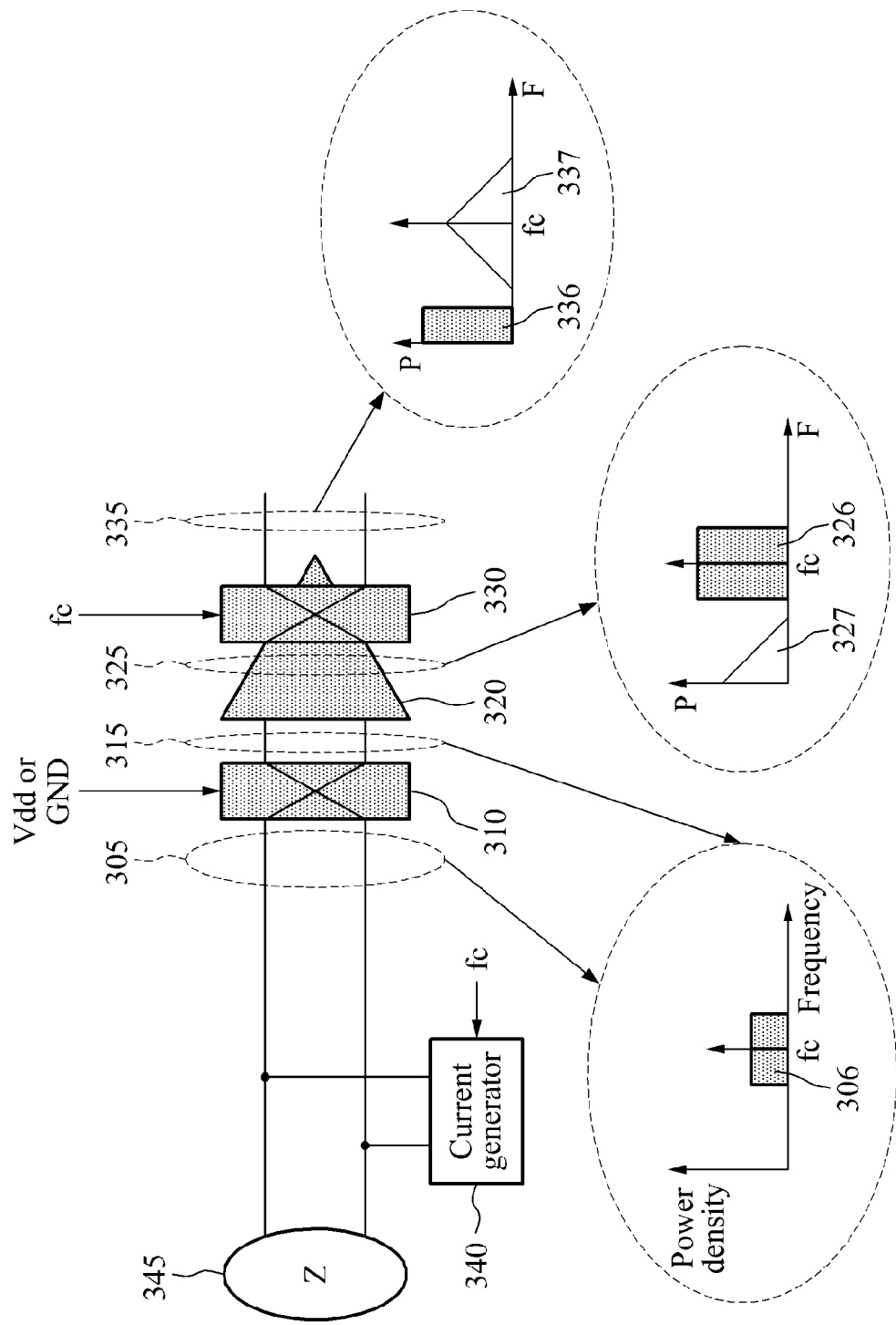
FIG. 3 is a diagram illustrating an example of an operation of a measuring apparatus that measures impedance.

FIG. 3 illustrates an example of an operation of a measuring apparatus 300 that measures impedance. Referring to FIG. 3, the measuring apparatus 300 includes a first chopper 310, an amplifier 320, and a second chopper 330. Although not shown in FIG. 3, the measuring apparatus 300 further includes a controller configured to control the first chopper 310 and the second chopper 330.

Hereinafter, bypass, amplification, and demodulation of an input signal passing the first chopper 310, the amplifier 320, and the second chopper 330 in an impedance measurement mode will be described in detail. In each graph shown in FIG. 3, an x-axis denotes a frequency, and a y-axis denotes a power density.

The measuring apparatus 300 receives an input signal for impedance measurement, through an input end 305. Hereinafter, the input signal for impedance measurement will be referred to as an impedance signal. The impedance signal includes information of a potential difference occurring when a current generated by a current generator 340 flows into a human body 345 that is modeled as impedance Z. The current generator 340 generates an AC of a frequency fc.

Since the impedance signal has the frequency fc as a central frequency, the impedance signal may be expressed similar to a signal 306 in a graph corresponding to the input end 305. Since a level of the current flowing in the human body 345 is low, a power density of the impedance signal is also low. In order to measure the impedance signal, the impedance signal is amplified by the amplifier 320.

1/f noise occurs in the amplifier 320. However, the frequency fc used for impedance measurement is positioned out of a band of the 1/f noise on a frequency domain. In this example, the impedance signal may be free from interference of the 1/f noise, and the first chopper 310 may not need to modulate the impedance signal to prevent the interference of the 1/f noise. The controller controls the first chopper 310 for the impedance signal to bypass the first chopper 310. For example, the controller may provide a constant voltage signal of Vdd or a ground GND to the first chopper 310. When the impedance signal bypasses the first chopper 310, the impedance signal before passing through the first chopper 310 may be substantially identical to the impedance signal after passing through the first chopper 310. The impedance signal may be expressed similar to the signal 306 in the graph corresponding to a node 315 between the first chopper 310 and the amplifier 320.

The impedance signal is amplified by the amplifier 320. The impedance signal may be expressed similar to a signal 326 in a graph corresponding to an internal portion 325 of the amplifier 320. The power density of the impedance signal increases when the impedance signal passes through the amplifier 320. The 1/f noise may be expressed similar to a signal 327 in the graph corresponding to the internal portion 325 of the amplifier 320. The 1/f noise occurs in a low-frequency band. The signal 326 and the signal 327 may not overlap in the graph corresponding to the internal portion 325 of the amplifier 320, which means that the impedance signal may be free from the interference of the 1/f noise, since the impedance signal has the frequency fc as the center frequency.

The controller controls the second chopper 330 to demodulate the amplified signal 326. In detail, the controller provides a signal having the frequency fc to the second chopper 330. In this example, referring to a graph corresponding to an output end 335, the impedance signal passes through the second chopper 330 to be demodulated to a signal 336. Simultaneously, a signal corresponding to the 1/f noise passes through the second chopper 330 to be modulated to a signal 337 having the frequency fc as a center frequency. The signal 336 and the signal 337 may not overlap in the graph corresponding to the output end 335, which means that the impedance signal may be free from the interference of the 1/f noise, since the impedance signal is demodulated by the second chopper 330 and simultaneously, the 1/f noise is modulated by the second chopper 330. As described above, the measuring apparatus 300 may provide technology that controls the first chopper 310 and the second chopper 330 for the impedance signal to be amplified without being affected by the 1/f noise.

Figure 4:
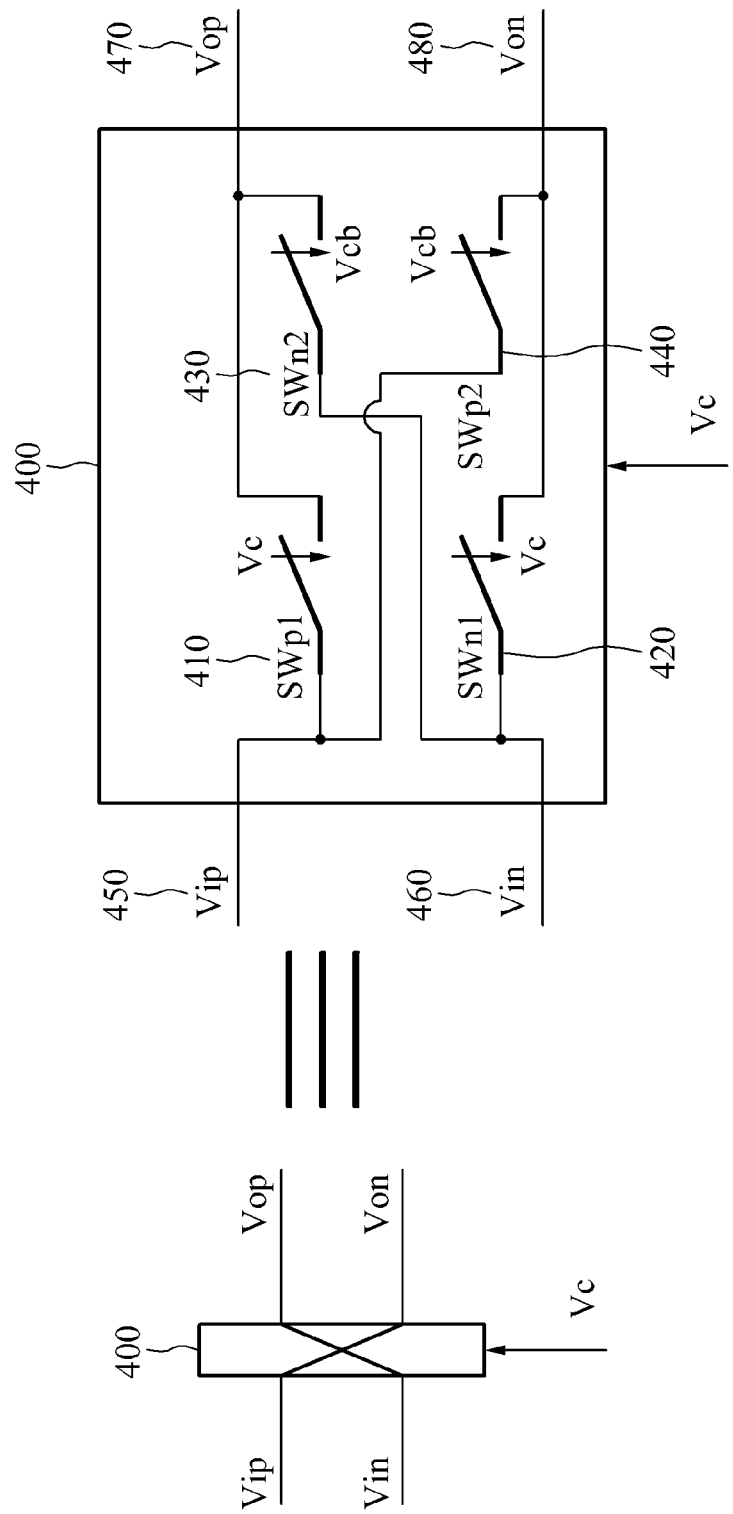
FIG. 4 is a circuit diagram illustrating an example of a chopper.

FIG. 4 illustrates an example of a chopper 400. Referring to FIG. 4, the chopper 400 connects input ports 450 and 460 to output ports 470 and 480, based on a control voltage Vc. The chopper 400 includes a first switch 410 SWp1, a second switch 420 SWn1, a third switch 430 SWn2, and a fourth switch 440 SWp2 that are operated based on the control voltage.

The first switch 410, the second switch 420, the third switch 430, and the fourth switch 440 may be turned on when a control voltage is logically "1", and be turned off when a control voltage is logically "0". In FIG. 4, a control voltage Vcb that controls the third switch 430 and the fourth switch 440 is a voltage logically inverted from the control voltage Vc.

When the control voltage Vc is logically "1" and the control voltage Vcb is logically "0", the first switch 410 and the second switch 420 may be turned on, and the third switch 430 and the fourth switch 440 may be turned off. In this example, the first input port 450 may be connected to the first output port 470, and the second input port 460 may be connected to the second output port 480. A state in which the first input port 450 is connected to the first output port 470 and the second input port 460 is connected to the second output port 480 may be referred to as a first state. In the first state, Vip=Vop, and Vin=Von.

Conversely, when the control voltage Vc is logically "0" and the control voltage Vcb is logically "1", the first switch 410 and the second switch 420 may be turned off, and the third switch 430 and the fourth switch 440 may be turned on. In this example, the first input port 450 may be connected to the second output port 480, and the second input port 460 may be connected to the first output port 470. A state in which the first input port 450 is connected to the second output port 480 and the second input port 460 is connected to the first output port 470 may be referred to as a second state. In the second state, Vip=Von, and Vin=Vop.

The controller 140 of FIG. 1 may provide an AC voltage or a DC voltage to the chopper 400, based on a measurement mode. When an AC voltage is provided as the control voltage Vc of the chopper 400, the chopper 400 may switch between the first state and the second state, at every interval of the control voltage. For example, when the control voltage corresponds to an AC voltage of 1 kHz, the interval of the control voltage may correspond to 1 millisecond (ms). In this example, the chopper 400 may switch between the first state and the second state at every 1 ms. In detail, the chopper 400 may be operated in the first state for 0.5 ms, operated in the second state for subsequent 0.5 ms, and operated in the first state again for subsequent 0.5 ms.

When an AC voltage is provided to the chopper 400, the chopper 400 may modulate or demodulate an input signal based on a frequency of the AC voltage. For example, the chopper 400 may switch a signal applied to the first input port 450 and a signal applied to the second input port 460 based on the interval of the control voltage Vc, and output the signals through the first output port 470 and the second output port 480. In this example, the input signal may be modulated to a signal having a frequency of the control voltage Vc as a center frequency. When the input signal corresponds to a signal having the frequency of the control voltage Vc as a center frequency, a frequency component of the control voltage Vc included in the input signal may be removed by the chopper 400. In this example, the input signal may be demodulated to a signal not having the frequency component of the control voltage Vc.

When a DC voltage is provided as the control voltage Vc of the chopper 400, the chopper 400 may be operated in one of the first state and the second state, based on a logical value of the DC voltage. For example, when the control voltage corresponds to a DC voltage of Vdd that is logically "1", the chopper 400 may be operated in the first state. When the control voltage corresponds to a DC voltage of GND that is logically "0", the chopper 400 may be operated in the second state.

When a DC voltage is provided to the chopper 400, the input single may bypass the chopper 400. For example, the chopper 400 may maintain the first state or the second state based on the control voltage Vc. When the control voltage Vc is logically "1", the chopper 400 may maintain the first state, and thus, the input signal may bypass the chopper 400. When the control voltage Vc is logically "0", the chopper 400 may maintain the second state, and thus, voltages applied to the input ports 450 and 460 may be switched and output.

Although an example of the chopper 400 implemented to control a flow of an electric signal based on the control voltage Vc has been described above, a configuration of the chopper 400 is not limited to the example. Depending on an example, the configuration of the chopper 400 may be changed variously. For example, the chopper 400 may further include a capacitor at each output end, and an output value may be determined based on an amount of electric charge accumulated in each capacitor.

Figure 5:
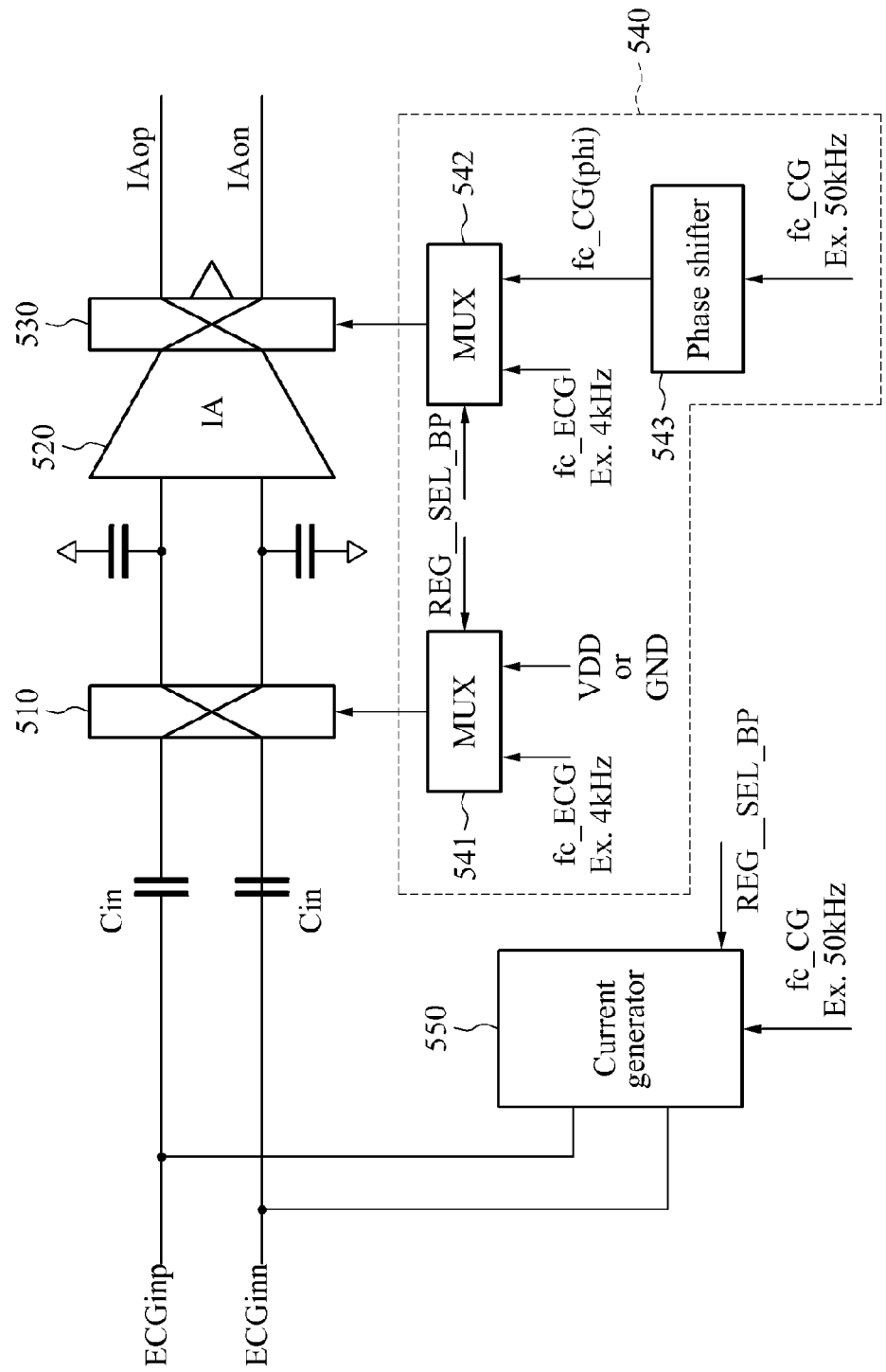
FIG. 5 is a circuit diagram illustrating an example of a controller.

FIG. 5 illustrates an example of a controller 540. Referring to FIG. 5, a measuring apparatus 500 includes a first chopper 510, an amplifier 520, and a second chopper 530. The descriptions provided with reference to FIGS. 1 through 4 may apply to each of the first chopper 510, the amplifier 520, and the second chopper 530.

The measuring apparatus 500 further includes the controller 540, and the controller 540 is implemented using multiplexers (MUXes). In this example, the controller 540 includes a first MUX 541 for the first chopper 510, and a second MUX 542 for the second chopper 530. The first MUX 541 provides a control voltage to the first chopper 510, and the second MUX 542 provides a control voltage to the second chopper 530.

The controller 540 controls the first MUX 541 and the second MUX 542, based on a measurement mode. For example, in a biopotential measurement mode, the controller 540 may control the first MUX 541 and the second MUX 542 to provide, to the first chopper 510 and the second chopper 530, respectively, a frequency signal to be used to modulate and demodulate a biopotential signal. In an impedance measurement mode, the controller 540 may control the first MUX 541 to provide, to the first chopper 510, a constant voltage signal to be used to have an impedance signal bypass the first chopper 510. The controller 540 may also control the second MUX 542 to provide, to the second chopper 530, a frequency signal to be used to demodulate the impedance signal.

The first MUX 541 receives a constant voltage signal Vdd or GND and a frequency signal to be used to modulate the biopotential signal. For example, the first MUX 541 may receive a first input signal corresponding to the frequency signal to be used to modulate the biopotential signal, and receive a second input signal corresponding to the constant voltage signal. The frequency signal to be used to modulate the biopotential signal may correspond to 4 kHz.

The controller 540 controls the first MUX 541, using a register REG_SEL_BP. The register REG_SEL_BP is set to be a value indicating the measurement mode. For example, when the register REG_SEL_BP is set to "1", the REG_SEL_BP may indicate the biopotential measurement mode. When the REG_SEL_BP is set to "0", the register REG_SEL_BP may indicate the impedance measurement mode. The controller 540 provides the register REG_SEL_BP as a selection signal of the first MUX 541.

When the register REG_SEL_BP indicates the biopotential measurement mode, the first MUX 541 outputs the frequency signal to be used to modulate the biopotential signal. When the register REG_SEL_BP indicates the impedance measurement mode, the first MUX 541 outputs the constant voltage signal to be used to have the impedance signal bypass the first chopper 510. The signal output by the first MUX 541 is provided as the control voltage of the first chopper 510, and an operation of the first chopper 510 is controlled by the control voltage.

The second MUX 542 receives the frequency signal to be used to demodulate the biopotential signal and a phase-shifted frequency signal to be used to demodulate the impedance signal. For example, the second MUX 542 may receive a first input signal corresponding to the frequency signal to be used for demodulating the biopotential signal, and receive a second input signal corresponding to the frequency signal to be used for demodulating the impedance signal. The frequency signal to be used for demodulating the biopotential signal may correspond to 4 kHz, and the frequency signal to be used for demodulating the impedance signal may correspond to 50 kHz.

The controller 540 controls the second MUX 542, using the register REG_SEL_BP indicating the measurement mode. The controller 540 provides the register REG_SEL_BP as a selection signal of the second MUX 542. The controller 540 may simultaneously control the first MUX 541 and the second MUX 542, using the identical register REG_SEL_BP.

When the register REG_SEL_BP indicates the biopotential measurement mode, the second MUX 542 outputs the frequency signal to be used to demodulate the biopotential signal. When the register REG_SEL_BP indicates the impedance measurement mode, the second MUX 542 outputs the phase-shifted frequency signal to be used to demodulate the impedance signal. The signal output by the second MUX 542 is provided as the control voltage of the second chopper 530, and an operation of the second chopper 530 is controlled by the control voltage.

The measuring apparatus 500 measures an impedance value of a real number component and an impedance value of an imaginary number component, by adjusting a phase of a frequency signal to be used to demodulate the impedance signal. For example, the measuring apparatus 500 may obtain the impedance value of the real number component, by demodulating the impedance signal, using a frequency signal of a phase θ degrees (°). The measuring apparatus 500 may obtain the impedance value of the imaginary number component, by demodulating the impedance signal, using a frequency signal of a phase 90°.

To achieve the foregoing, the controller 540 further includes a phase shifter 543. The phase shifter 543 adjusts the phase of the frequency signal to be used to demodulate the impedance signal. For example, the phase shifter 543 may shift 90° the phase of the frequency signal to be used to demodulate the impedance signal. The phase-shifted frequency signal is input as the second input signal of the second MUX 542.

The controller 540 may control the phase shifter 543, using a register for phase shifting. The controller 540 may determine a phase angle to be shifted based on a value of the register, and control the phase shifter 543 to shift the phase based on the determined size. For example, when the register for phase shifting is set to be a value indicating a phase 0°, the controller 540 may control the phase shifter 543 for the frequency signal to be used to demodulate the impedance signal to bypass the phase shifter 543. When the register for phase shifting is set to be a value indicating a phase 90°, the controller 540 may control the phase shifter 543 to shift 90° the frequency signal to be used to demodulate the impedance signal.

Although FIG. 5 illustrates the controller 540 that includes the first MUX 541, the second MUX 542, and the phase shifter 543, the configuration of the controller 540 may be changed variously. For example, the measuring apparatus 500 may include the first MUX 541, the second MUX 542, and the phase shifter 543 as separate elements distinct from the controller 540. In this example, the controller 540 may generate a control signal to control the first MUX 541, the second MUX 542, and the phase shifter 543.

The controller 540 also generates a control signal to control a current generator 550 for impedance measurement. When the measurement mode corresponds to the biopotential measurement mode, the controller 540 generates the control signal to deactivate the current generator 550. When the measurement mode corresponds to the impedance measurement mode, the controller 540 generates the control signal to activate the current generator 550.

The controller 540 controls the current generator 550, using the register REG_SEL_BP indicating the measurement mode. That is, the controller 540 provides the register REG_SEL_BP indicating the measurement mode to the current generator 550. The current generator 550 is activated or deactivated based on the value of the register REG_SEL_BP indicating the measurement mode. When the value of the register REG_SEL_BP that is provided to the current generator 550 is "1", the measuring apparatus 500 may be operated in the biopotential measurement mode, and thus, the current generator 550 may be deactivated. Conversely, when the value of the register REG_SEL_BP that is provided to the current generator 550 is "0", the measuring apparatus 500 may be operated in the impedance measurement mode, and thus, the current generator 550 may be activated to generate a current for impedance measurement.

The current generator 550 receives an AC signal having a frequency for impedance measurement, e.g., the frequency signal to be used to demodulate the impedance signal. The current generator 550 generates an AC current for impedance measurement, using the received AC signal. The AC signal may be externally input, or depending on example, may be provided by the controller 540.

As another example, the controller 540 may provide, to the first chopper 510 for impedance measurement, a frequency signal to be used to modulate the impedance signal, in lieu of the constant voltage signal. For example, when a frequency of the AC current for impedance measurement is included within a band of 1/f noise of the amplifier 520, the impedance signal may be subject to interference of the 1/f noise. In order to prevent the impedance signal from being subject to the interference of the 1/f noise, the controller 540 may control the first MUX 541 and the second MUX 542 to provide, to the first chopper 510 and the second chopper 530, respectively, the frequency signal to be used to modulate and demodulate the impedance signal.

The first MUX 541 may receive the frequency signal to be used to modulate the impedance signal and the constant voltage signal to be used to have the impedance signal bypass the first chopper 510. For example, the first MUX 541 may receive a first input signal corresponding to the frequency signal to be used to modulate the impedance signal, and a second input signal corresponding to the constant voltage signal. The frequency signal to be used to modulate the impedance signal may be identical to the frequency signal to be used to modulate the biopotential signal described above.

The controller 540 may control the first MUX 541, using the register REG_SEL_BP. As described above, when the register REG_SEL_BP is set to "1", the register REG_SEL_BP may indicate the biopotential measurement mode. When the register REG_SEL_BP is set to "0", the register REG_SEL_BP may indicate the impedance measurement mode. However, when the frequency of the AC current for impedance measurement is included within the band of the 1/f noise of the amplifier 520, the register REG_SEL_BP may be set to "1". Thus, the first MUX 541 and the second MUX 542 may provide the frequency signal to be used to modulate and demodulate the impedance signal to the first chopper 510 and the second chopper 530, respectively.

When the frequency of the AC current for impedance measurement is included within the band of the 1/f noise of the amplifier 520, the register REG_SEL_BP may be set to "2", not "1" or "0". When "2" is received as the selection signal, the first MUX 541 and the second MUX 542 may output the frequency signal to be used to modulate and demodulate the impedance signal to the first chopper 510 and the second chopper 530, respectively.

The operation of the controller 540 described above may be arranged as shown in Table 1.

TABLE 1

| Case | Measurement mode | First chopper 510 | Second chopper 530 |
|---|---|---|---|
| Case 1 | Biopotential measurement | fc_ECG | fc_ECG |
|  | Impedance measurement | DC (Vdd or GND) | fc_CG |
| Case 2 | Biopotential measurement | fc_ECG | fc_ECG |
|  | Impedance measurement | fc_ECG | fc_ECG |

In Table 1, fc_ECG denotes a frequency of the frequency signal to be used to modulate and demodulate the biopotential signal and/or the impedance signal, DC denotes the DC voltage, and fc_CG denotes a frequency of the frequency signal to be used to demodulate the impedance signal.

Case 1 corresponds to an example in which the frequency fc_CG is higher than the band of the 1/f noise of the amplifier 520. For example, in Case 1, fc_CG=50 kHz, and fc_ECG=4 kHz. In the biopotential measurement mode of Case 1, the controller 540 may provide the frequency fc_ECG to both of the first chopper 510 and the second chopper 530. In the impedance measurement mode of Case 1, the controller 540 may provide the DC voltage DC to the first chopper 510, and the frequency fc_CG to the second chopper 530.

Case 2 corresponds to an example in which the frequency fc_CG is within the band of the 1/f noise of the amplifier 520. For example, in Case 2, fc_CG=50 Hz, and fc_ECG=4 kHz. In the biopotential measurement mode of Case 2, the controller 540 may provide the frequency fc_ECG to both the first chopper 510 and the second chopper 530. In the impedance measurement mode of Case 2, the controller 540 may provide the frequency fc_ECG to both the first chopper 510 and the second chopper 530.

In the impedance measurement mode of Case 2, an output signal of the second chopper 530 may have the frequency fc_CG, which corresponds to a modulated signal. In Case 2, the frequency fc_CG may be lower than a sampling frequency of an analog-to-digital converter (ADC) of the measuring apparatus 500. Thus, the ADC may perform analog-to-digital conversion on the output signal modulated to the frequency fc_CG, and the measuring apparatus 500, namely, a demodulator, may demodulate the output signal modulated to the frequency fc_CG through digital signal processing. The measuring apparatus 500 may further include a third chopper configured to demodulate the output signal to the frequency fc_CG. In this example, the controller 540 may provide the frequency fc_CG to the third chopper in the impedance measurement mode of Case 2. The third chopper may be controlled for an input signal to bypass the third chopper, in remaining modes excluding the impedance measurement mode of Case 2. To achieve the foregoing, the controller 540 may provide the DC voltage DC to the third chopper, in the remaining modes excluding the impedance measurement mode of Case 2.

Figure 6:
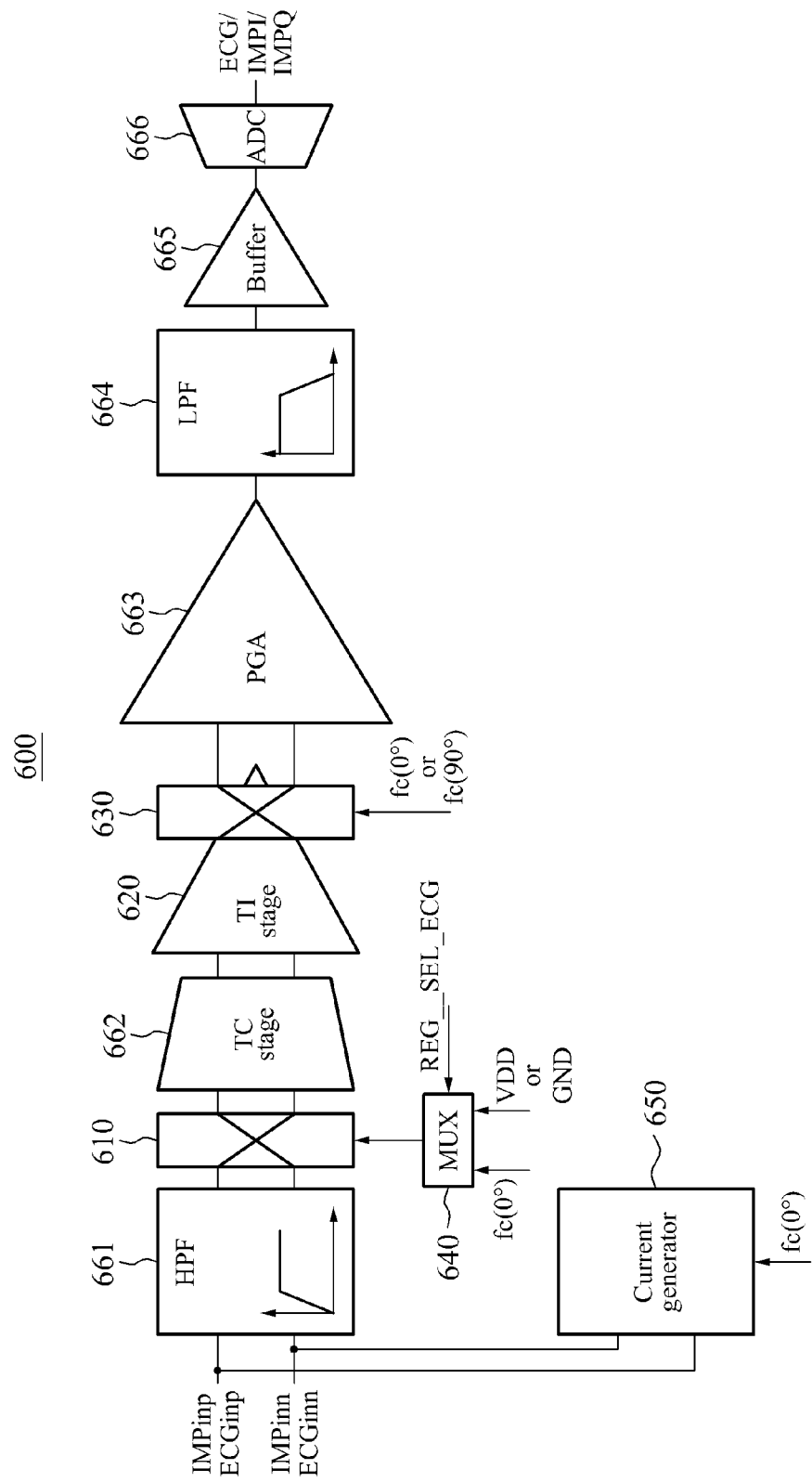
FIGS. 6 and 7 are block diagrams illustrating examples of measuring systems using a reconfigurable measuring apparatus.
Figure 7:
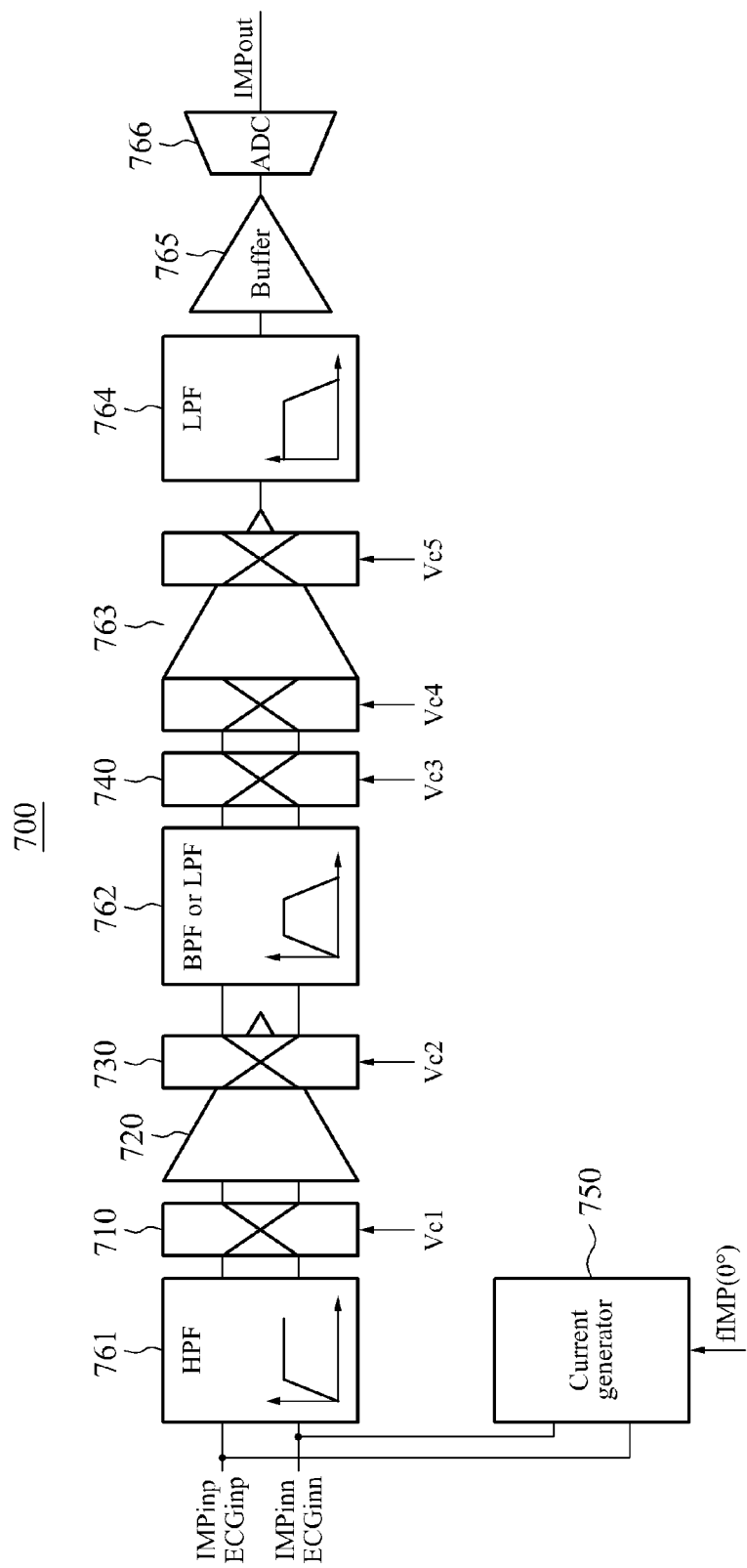

FIGS. 6 and 7 illustrate examples of measuring systems using a reconfigurable measuring apparatus. Referring to FIG. 6, a measuring apparatus 600 according to an example includes a first chopper 610, an amplifier 620 corresponding to, for example, a trans-impedance (TI) stage, a second chopper 630, a MUX 640, and a current generator 650. The descriptions provided with reference to FIGS. 1 through 5 may apply to the first chopper 610, the amplifier 620, the second chopper 630, the MUX 640, and the current generator 650. Although not shown in the drawings, the measuring apparatus 600 may further include a second MUX for the second chopper 630, and generate a control signal to control the MUX 640, the second MUX, and the current generator 650, depending on a measurement mode.

The measuring apparatus 600 further includes a high-pass filter (HPF) 661. The HPF 661 passes a signal of a band higher than or equal to a predetermined frequency, and blocks a signal of a band lower than the predetermined frequency. The measuring apparatus 600 may block a DC offset voltage, using the HPF 661. As to be described in detail, the amplifier 620 has an operating voltage range in which an input signal may be amplified in a desired ratio. When the DC offset voltage is included in an input voltage, the input voltage may be out of the operating voltage range. When the input voltage is out of the operating voltage range, the measuring apparatus 600 may be operated abnormally, for example, an output voltage may be saturated. The measuring apparatus 600 may prevent the abnormal operation of the measuring apparatus 600, using the HPF 661.

The measuring apparatus 600 further includes a transconductance (TC) amplifier 662 corresponding to, for example, a TC stage. The TC amplifier 662 outputs a current proportional to an input voltage. In detail, the higher the input voltage, the greater the current is output. The lower the input voltage, the lesser the current is output. The amplifier 620 interoperates with the TC amplifier 662. The amplifier 620 performs a TI amplification function. That is, the amplifier 620 outputs a voltage proportional to an input current. In detail, the greater the current output by the TC amplifier 662, the higher the voltage is output. The lesser the current output by the TC amplifier 662, the lower the voltage is output.

The measuring apparatus 600 further includes a second amplifier 663. The second amplifier 663 is an amplifier of which a gain is adjustable, and may include, for example, a programmable gain amplifier (PGA). Using the second amplifier 663, the measuring apparatus 600 secondarily amplifies the signal amplified by the amplifier 620. A suitable range of an output signal of the second amplifier 663 may differ depending on an application that receives the output signal. For example, a first application may receive 0 volts (V) to 5 V, whereas a second application may receive 0 V to 20 V. The measuring apparatus 600 controls the gain of the second amplifier 663 so that the output signal may be output within a voltage range suitable for an application.

The measuring apparatus 600 further includes a low-pass filter (LPF) 664. The LPF 664 passes a signal of a band lower than or equal to a predetermined frequency, and blocks a signal of a band higher than the predetermined frequency. The measuring apparatus 600 may remove high-frequency noise, using the LPF 664.

The measuring apparatus 600 further includes a buffer 665. The buffer 665 enables a sufficient current to be supplied to an ADC 666, in response to an input load of the ADC 666.

The measuring apparatus 600 further includes the ADC 666. The ADC 666 converts an analog electric signal to a digital electric signal. The measuring apparatus 600 converts an amplified analog signal to a digital signal, using the ADC 666, and outputs the digital signal.

Referring to FIG. 7, a measuring apparatus 700 according to another example includes a first chopper 710, an amplifier 720, a second chopper 730, and a current generator 750. The descriptions provided with reference to FIGS. 1 through 5 may apply to the first chopper 710, the amplifier 720, the second chopper 730, and the current generator 750. Although not shown in the drawings, the measuring apparatus 700 may further include a controller, and the controller may control the first chopper 710, the amplifier 720, the second chopper 730, and the current generator 750, depending on a measurement mode.

The measuring apparatus 700 further includes an HPF 761. The measuring apparatus 700 blocks a DC offset, using the HPF 761. By blocking the DC offset, using the HPF 761, the measuring apparatus 700 may prevent an abnormal operation of the amplifier 720.

The measuring apparatus 700 may further include a band-pass filter (BPF) 762. The BPF 762 may pass a signal of a predetermined frequency band, and blocks a signal of bands other than the predetermined frequency band. The measuring apparatus 700 may remove high-frequency noise and low-frequency noise, using the BPF 762. In another example, the BPF 762 may be replaced with an LPF. In this example, the measuring apparatus 700 may remove high-frequency noise, using the LPF.

The measuring apparatus 700 further includes a third chopper 740. Referring to Table 1, in the impedance measurement mode of Case 2, the controller may provide frequency signals to be used to modulate and demodulate an impedance signal to the first chopper 710 and the second chopper 730, respectively. The impedance signal may be modulated to the frequency fc_ECG by the first chopper 710, amplified by the amplifier 720, and demodulated to the frequency fc_ECG by the second chopper 730. The impedance signal demodulated by the second chopper 730 may still correspond to the signal modulated to the frequency fc_CG. Accordingly, the controller may provide the frequency fc_CG to the third chopper 740 so that the signal may be demodulated to the frequency fc_CG by the third chopper 740.

Conversely, in the remaining modes excluding the impedance measurement mode of Case 2, the controller may provide the DC voltage DC to the third chopper 740. In this example, an input signal may bypass the third chopper 740.

The measuring apparatus 700 further includes a second amplifier 763, an LPF 764, a buffer 765, and an ADC 766. The descriptions provided with reference to FIG. 6 may apply to the second amplifier 763, the LPF 764, the buffer 765, and the ADC 766, and thus, duplicated descriptions will be omitted for conciseness.

Figure 8A:
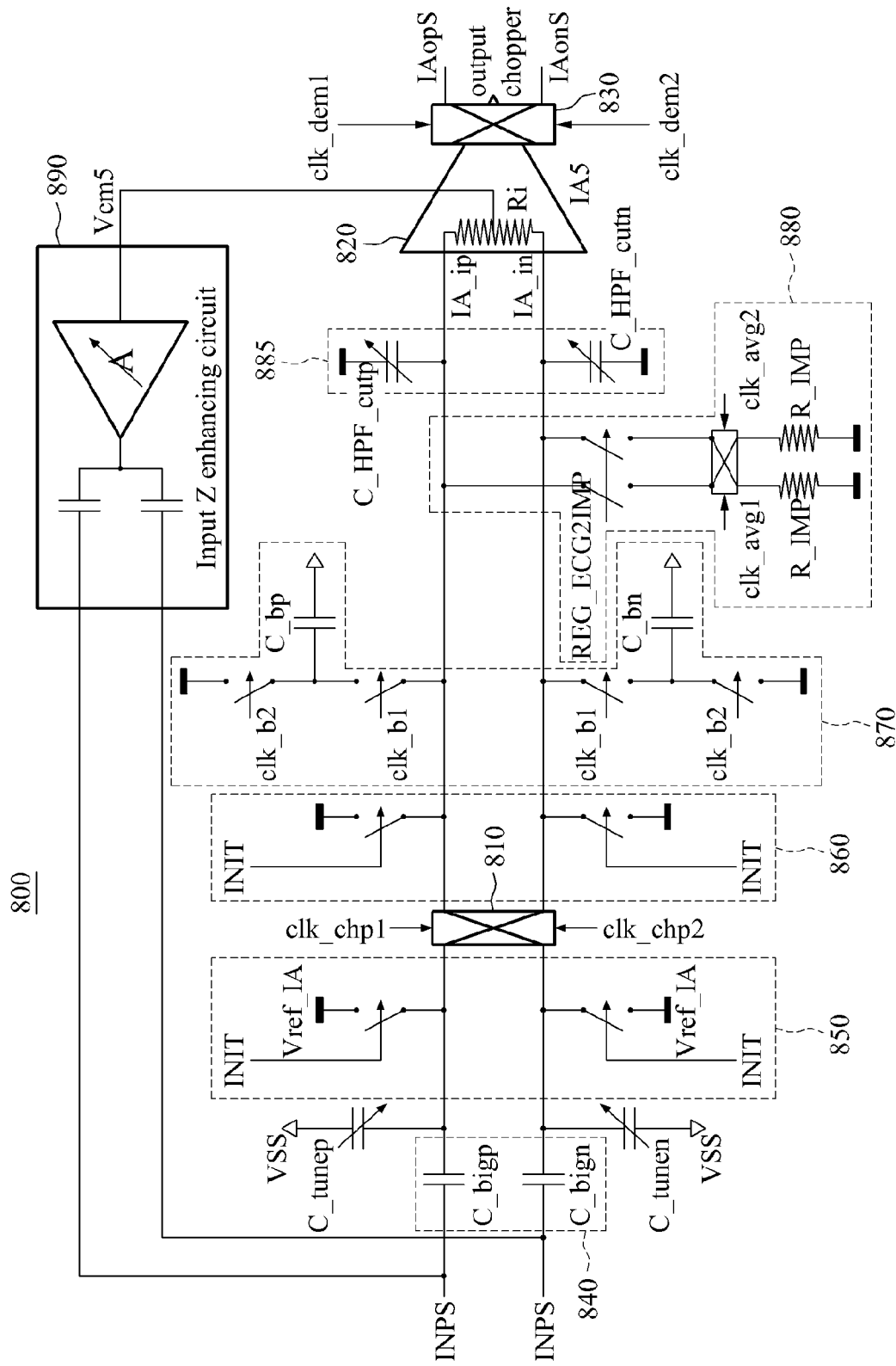
FIGS. 8A through 8D are circuit diagrams illustrating an example of an input end of a measuring apparatus.

FIGS. 8A through 8D illustrate an example of an input end of a measuring apparatus 800. Referring to FIG. 8A, the measuring apparatus 800 includes a first chopper 810, an amplifier 820, and a second chopper 830. The descriptions provided with reference to FIGS. 1 through 7 may apply to the first chopper 810, the amplifier 820, and the second chopper 830.

The measuring apparatus 800 further includes a first capacitor unit 840, a first resistance unit 870, a second resistance unit 880, and a second capacitor unit 885. The first capacitor unit 840, the first resistance unit 870, the second resistance unit 880, and the second capacitor unit 885 implements a resistance component and a capacitor component that constitute an HPF, and provides a bias voltage to an input of the amplifier 820. The HPF filters a DC offset voltage, and the bias voltage provided to the input of the amplifier 820 enables the amplifier 820 to be operated within a normal operating range.

In a biopotential measurement mode, the first resistance unit 870 is activated to provide the bias voltage to the input of the amplifier 820. In the biopotential measurement mode, a combination of the first chopper 810 and the second capacitor unit 885 implements the resistance component of the HPF. The first capacitor unit 840 implements the capacitor component of the HPF.

In an impedance measurement mode, since the first chopper 810 acts as a conducting wire, the second capacitor unit 885 does not correspond to the resistance component. Accordingly, the second resistance unit 880 is activated, whereby the resistance component of the HPF is implemented. The first capacitor unit 840 implements the capacitor component of the HPF. In the impedance measurement mode, the second resistance unit 880 provides the bias voltage to the input of the amplifier 820. Operations of the first resistance unit 870 and the second resistance unit 880 will be described hereinafter in detail with reference to FIGS. 8C and 8D.

The measuring apparatus 800 further includes start-up circuits 850 and 860 to start up circuits included in the measuring apparatus 800. The amplifier 820 has a voltage range in which an input signal may be amplified in a desired ratio. Hereinafter, for ease of description, the voltage range of the amplifier 820 in which the input signal is amplified in the desired ratio will be referred to as a normal operating range.

In order for the amplifier 820 to be operated within the normal operating range in a transient state in which the measuring apparatus 800 switches from a turn-off state to a turn-on state, each of the start-up circuits 850 and 860 inputs a predetermined reference voltage. For example, the start-up circuit 850 provides the reference voltage as an input of the first chopper 810 for a short time. The start-up circuit 860 provides the reference voltage as an input of the amplifier 820. When the amplifier 820 is out of the unstable transient state, the start-up circuits 850 and 860 are deactivated.

According to another example, the start-up circuits 850 and 860 may be utilized for recovery of the amplifier 820. For example, when an input voltage sparks, a voltage component increasing rapidly may correspond to a high-frequency component, and thus, may not be filtered by the HPF of the input end. The voltage component increasing rapidly may be input into the amplifier 820, and the amplifier 820 may be saturated while amplifying the voltage component increasing rapidly. When the amplifier 820 is saturated, the amplifier 820 may not amplify the input voltage to be greater than a saturated voltage. It may be construed as that the input signal input into the amplifier 820 is out of the normal operating range due to the voltage component increasing rapidly.

When the amplifier 820 is saturated, the start-up circuits 850 and 860 may input the predetermined reference for the amplifier 820 to be operated within the normal operating range. From such a point of view, the start-up circuits 850 and 860 may also be referred to as recovery circuits.

The measuring apparatus 800 further includes an input impedance (Z) enhancing circuit 890. The input Z enhancing circuit 890 feeds back a portion of an output of the amplifier 820 to the input end, thereby enhancing an input impedance.

Figure 8B:
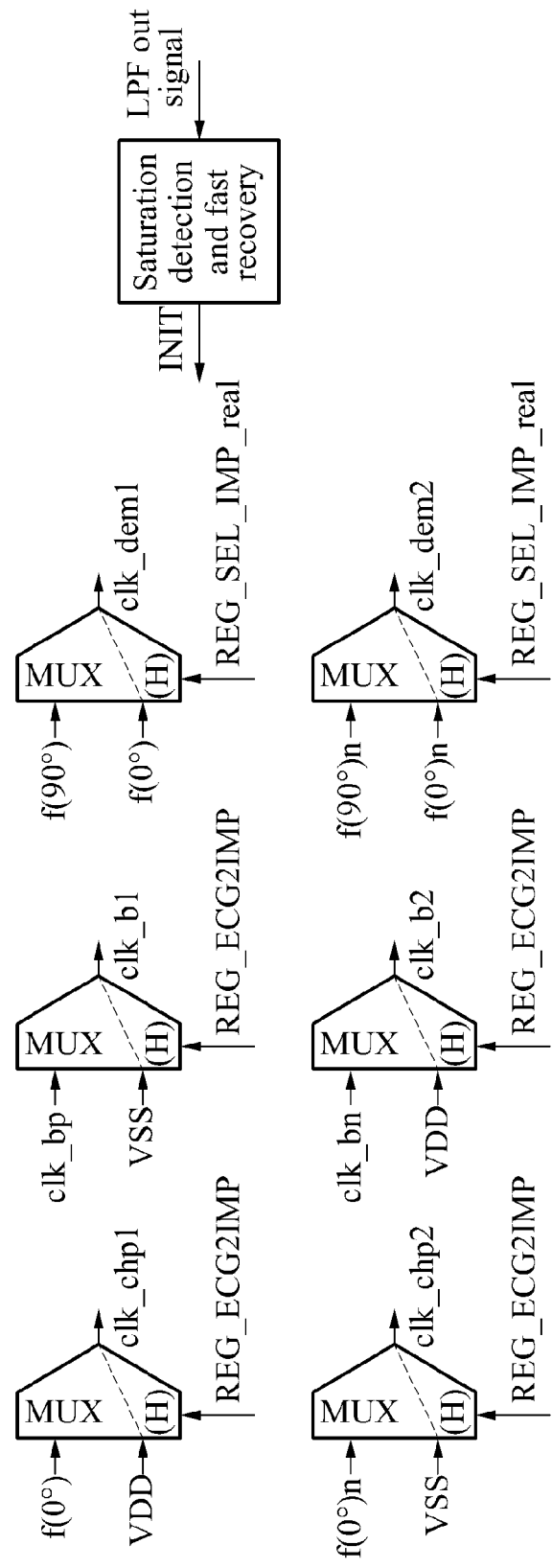

Referring to FIG. 8B, each of clock signals clk_chp1, clk_chp2, clk_b1, clk_b2, clk_dem1, and clk_dem2, as shown in FIG. 8A, are generated by a 2×1 MUX. Each MUX may be controlled by a register REG_ECG2IMP indicating a measurement mode, or a register REG_SEL_IMP_real indicating which one of a real number component and an imaginary component of the impedance signal is to be measured.

A control signal INIT to control the recovery circuits 850 and 860 is generated by a processor configured to perform a saturation detection and fast recovery function. The processor detects whether the amplifier 820 is saturated, based on an output of the LPF 664 of FIG. 6 or the LPF 764 of FIG. 7, and generates the control signal INIT.

Figure 8C:
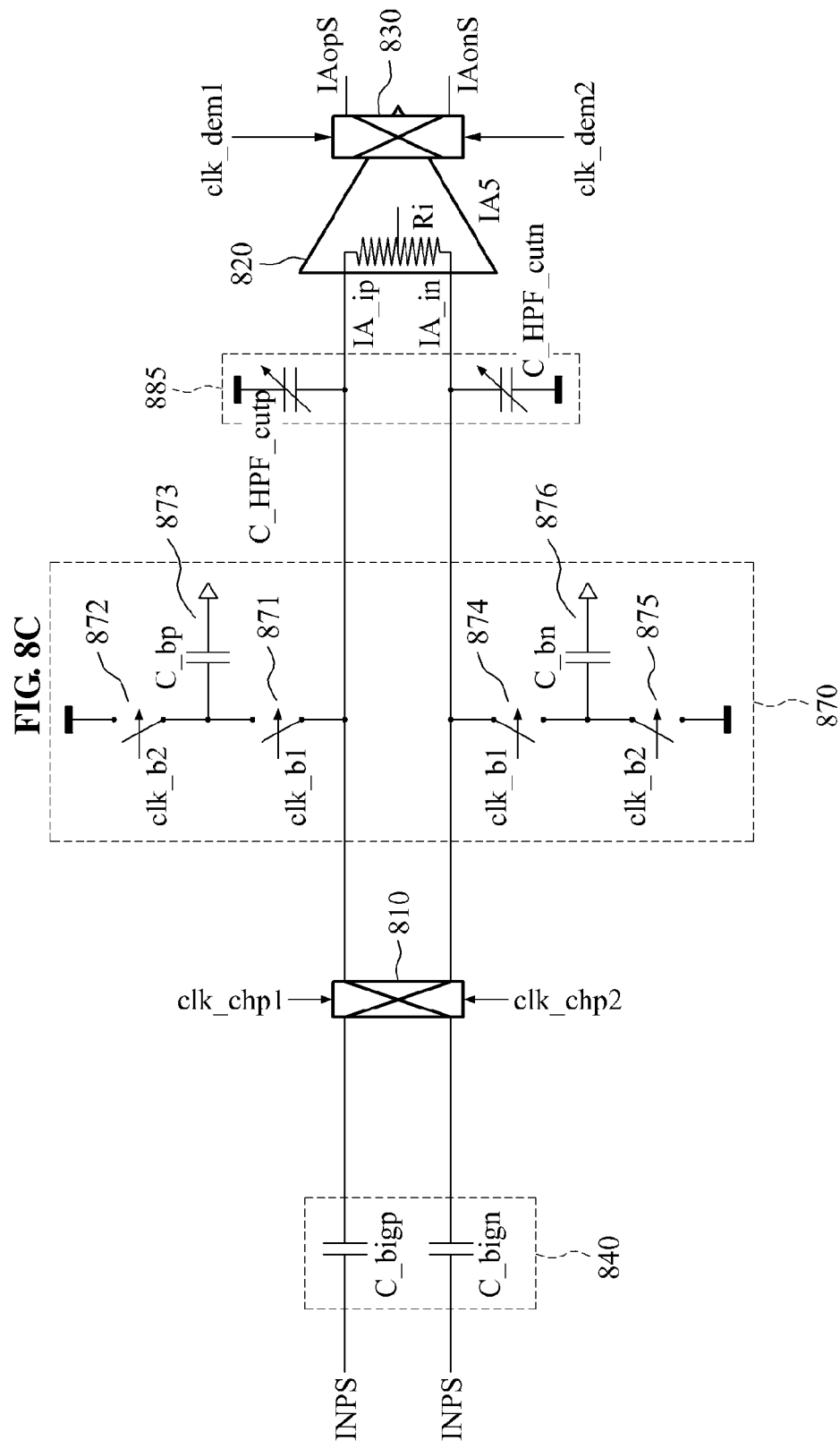

Referring to FIG. 8C, in the biopotential measurement mode, the first resistance unit 870 is activated. As to be described in detail hereinafter, the second capacitor unit 885 and the first chopper 810 implement the resistance component. Thus, the HPF is configured using a combination of the first capacitor unit 840, the first chopper 810, and the second capacitor unit 885.

In detail, the first resistance unit 870 is disposed at nodes between the first chopper 810 and the amplifier 820. The nodes between the first chopper 810 and the amplifier 820 include a first node and a second node. Depending on an example, the first node may be referred to as a positive node, and the second node may be referred to as a negative node. The amplifier 820 may be configured using a differential amplifier, and a voltage of the first node and a voltage of the second node are provided as a first input and a second input of the differential amplifier, respectively.

The first resistance unit 870 includes a first switch 871, a second switch 872, and a first capacitor 873. The first switch 871, the second switch 872, and the first capacitor 873 interoperate with one another, and act for a voltage value, for example, a bias voltage, suitable for an input voltage of the amplifier 820 to be applied to the first node. The bias voltage may have a preset voltage value, and depending on an example, may correspond to GND. A resistance value implemented by the first switch 871, the second switch 872, and the first capacitor 873 may be a value overly greater than a general resistance. Accordingly, the first resistance unit 870 may provide the bias voltage to the input of the amplifier 820, without substantially affecting a flow of a current in a circuit.

A control signal clk_b1 of the first switch 871 may correspond to a clock signal, and the control signal clk_b1 of the first switch 871 and a control signal clk_b2 of the second switch 872 have mutually exclusive values. For example, when the control signal clk_b1 is logically "1", the control signal clk_b2 is logically "0". When the control signal clk_b1 is logically "0", the control signal clk_b2 is logically "1". In other words, the first switch 871 and the second switch 872 are alternately turned on.

An amount of electric charge flowing per unit time between the first node and a node for the bias voltage may be determined based on a switching interval of the control signal clk_b1 and the control signal clk_b2 and a capacitance of the first capacitor 873. The amount of the electric charge flowing per unit time between the first node and the node for the bias voltage corresponds to a level of current. A potential difference between the bias voltage and the voltage of the first node corresponds to a level of voltage. When the level of current and the level of voltage are determined, a level of resistance may be determined. Based on the switching interval of the control signal clk_b1 and the control signal clk_b2 and the capacitance of the first capacitor 873, a first resistance component is implemented between the first node and the node for the bias voltage.

Similarly, the first resistance unit 870 includes a third switch 874, a fourth switch 875, and a second capacitor 876. The third switch 874, the fourth switch 875, and the second capacitor 876 implement a resistance component to supply a proper bias voltage to the second node. A second resistance component is implemented between the second node and the node for the bias voltage, based on the switching interval of the control signal clk_b1 and the control signal clk_b2 and a capacitance of the second capacitor 876.

The first chopper 810 is combined with a capacitance formed in an input terminal of the amplifier 820, and acts as an equivalent resistance. The first chopper 810 and the first capacitor unit 840 act as the HPF. The capacitance formed in the input terminal of the amplifier 820 mainly include a capacitance formed by the second capacitor unit 885, and a capacitance formed at a gate of an input end transistor, for example, a metal-oxide-semiconductor field-effect transistor (MOSFET), of the amplifier 820. By adjusting capacitance values of capacitors C_HPF_cutp and C_HPF_cutn included in the second capacitor unit 885, a cut-off frequency of an input HPF is adjusted. For example, the cut-off frequency of the input HPF may be adjusted to 0.5 Hz, 10 Hz, and/or other frequencies.

In the impedance measurement mode, the first switch 871 and the third switch 874 are turned off, and the first resistance unit 870 is deactivated.

Figure 8D:
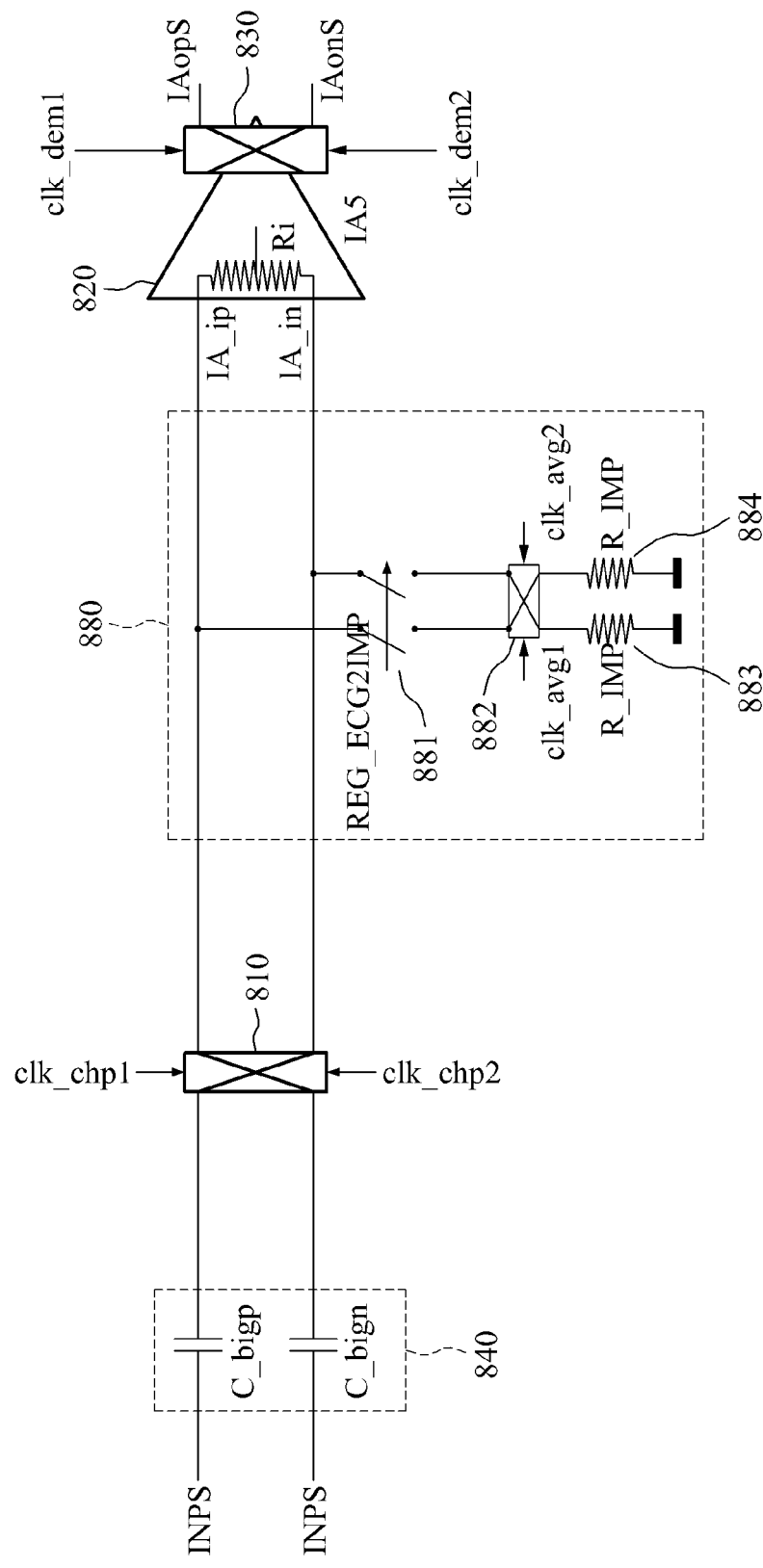

Referring to FIG. 8D, in the impedance measurement mode, the second resistance unit 880 is activated. As to be described in detail hereinafter, the second resistance unit 880 implements a resistance component. Accordingly, an HPF is configured using a combination of the second resistance unit 880 and the capacitor unit 840.

The second resistance unit 880 includes a switch 881, a chopper 882, a first resistor 883, and a second resistor 884. The switch 881 may activate and deactivate the second resistance unit 880. In the impedance measurement mode, when the switch 881 is turned on, the second resistance unit 880 is activated. In the biopotential measurement mode, when the switch 811 is turned off, the second resistance unit 880 is deactivated.

A resistance component corresponding to a constituent element of an HPF may be implemented differently in the biopotential measurement mode and the impedance measurement mode for the following reason. In the biopotential measurement mode, the first chopper 810 is operated, and thus, capacitances of the input end of the amplifier 820 and an action of the first chopper 810 are combined to act as an equivalent resistance. Accordingly, in the biopotential measurement mode, the HPF is formed using a combination of the capacitances of the input end of the amplifier 820 and the first chopper 810. Conversely, in the impedance measurement mode, the first chopper 810 performs a bypass function, and thus, the capacitances of the input end of the amplifier 820 do not act as an equivalent resistance. Accordingly, in the impedance measurement mode, separate resistors, for example, the first resistor 883 and the second resistor 884, are needed.

Since in the biopotential measurement mode a measurement band may correspond to a low frequency, a cut-off frequency of the HPF may be set to 0.5 Hz. In the impedance measurement mode, an input signal may be modulated based on a carrier frequency of a current applied to the current generator 750 of FIG. 7. Accordingly, a cut-off frequency of an input HPF may be associated with the carrier frequency. For example, when the frequency of the current applied to the current generator 750 corresponds to 50 kHz, the cut-off frequency of the input HPF in the impedance measurement mode may be set to 5 kHz.

The chopper 882, the first resistor 883, and the second resistor 884 may enable, to be substantially the same, a resistance implemented between the first node and the node for the bias voltage and a resistance implemented between the second node and the node for the bias voltage. Since physically different resistances are used for the first resistor 883 and the second resistor 884, a resistance value of the first resistor 883 and a resistance value of the second resistor 884 may not be substantially the same due to an error in a manufacturing process. The chopper 882 receives clock signals clk_avg1 and clk_avg2, and paths inside the chopper 882 are switched at every interval of the clock signals. Accordingly, although the first resistor 883 and the second resistor 884 may differ from each other due to a moderate error, resistance values of the first resistor 883 and the second resistor 884 are time-averaged, and the average resistance values of the first resistor 883 and the second resistor 884 are applied to the first node and the second node, respectively.

Figure 9:
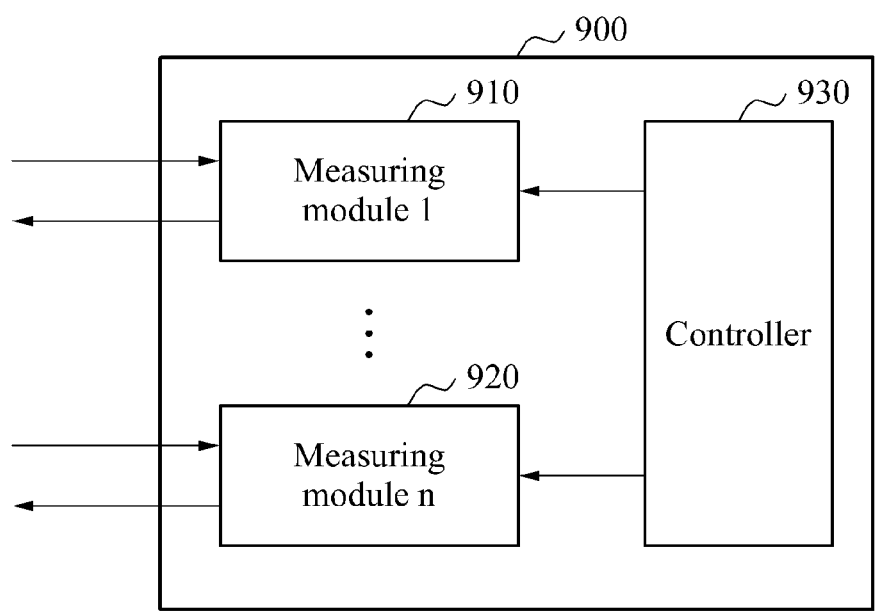
FIG. 9 is a block diagram illustrating an example of a measuring apparatus including a plurality of reconfigurable measuring modules.

FIG. 9 illustrates an example of a measuring apparatus 900 including a plurality of reconfigurable measuring modules. Referring to FIG. 9, the measuring apparatus 900 include a plurality of measuring modules, including a first measuring module 910 and an $n^{th}$ measuring module 920.

The measuring apparatus 900 controls the plurality of measuring modules based on a measurement mode of each of the plurality of measuring modules. For example, when the first measuring module 910 is operated in a biopotential measurement mode, a controller 930 included in the measuring apparatus 900 provides control signals for biopotential measurement to choppers included in the first measuring module 910. When the $n^{th}$ measuring module 920 is operated in an impedance measurement mode, the controller 930 provides control signals for impedance measurement to choppers included in the $n^{th}$ measuring module 920. The descriptions provided with reference to FIGS. 1 through 8 may apply to the plurality of measuring modules, and thus, duplicated descriptions will be omitted for conciseness.

Figure 10:
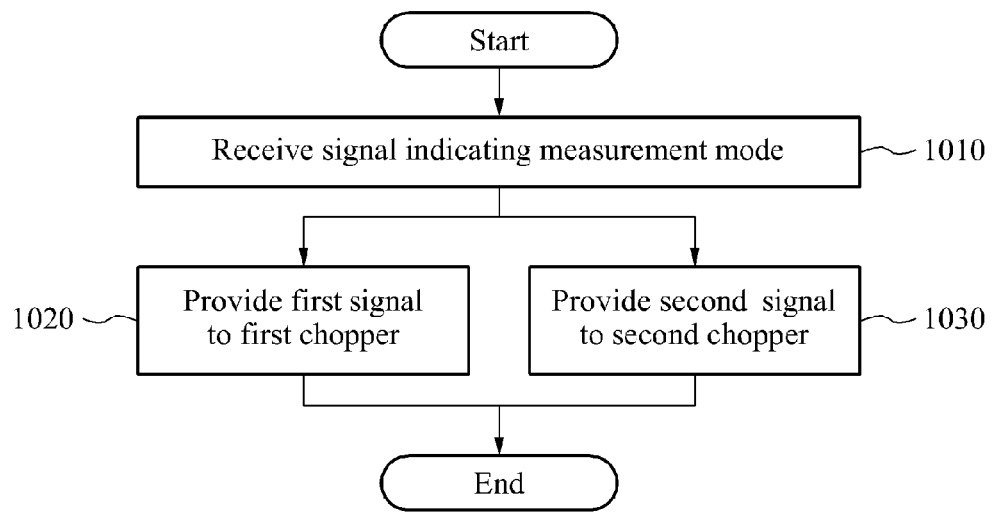
FIG. 10 is a flowchart illustrating an example of a method of controlling a reconfigurable measuring apparatus.

FIG. 10 illustrates an example of a method of controlling a reconfigurable measuring apparatus. Referring to FIG. 10, in operation 1010, the reconfigurable measuring apparatus receives a signal indicating a measurement mode. In operation 1020, the reconfigurable measuring apparatus provides a first signal to a first chopper. In operation 1030, the reconfigurable measuring apparatus provides a second signal to a second chopper.

Each operation included in the method of controlling the reconfigurable measuring apparatus may be performed by a controller included in the reconfigurable measuring apparatus. For example, in operation 1010, the controller may read a register value recorded in a register indicating the measurement mode. The descriptions provided with reference to FIGS. 1 through 8 may apply to each operation illustrated in FIG. 10, and thus, duplicated descriptions will be omitted for conciseness.

The various units, modules, elements, and methods described above may be implemented using one or more hardware components, one or more software components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A reconfigurable measuring apparatus comprising:
a first chopper configured to modulate an input signal;
an amplifier configured to amplify an output signal of the first chopper;
a second chopper configured to demodulate an output or internal signal of the amplifier; and
a controller configured to control the first chopper and the second chopper based on a measurement mode,
wherein the controller is configured to control the first chopper to modulate the input signal in response to the measurement mode being a biopotential measurement mode,
and wherein the controller is configured to control the first chopper to pass the input signal unmodulated in response to the measurement mode being an impedance measurement mode.

2. The apparatus of claim 1, wherein the measurement mode is selectively one of the biopotential measurement mode and the impedance measurement mode.

3. The apparatus of claim 1, wherein the controller is configured to:
provide a frequency signal corresponding to the biopotential measurement mode to the first chopper and the second chopper in response to the measurement mode being selected to be the biopotential measurement mode.

4. The apparatus of claim 1, wherein the controller is configured to:
provide a frequency signal corresponding to the impedance measurement mode to the second chopper in response to the measurement mode being selected to be the impedance measurement mode.

5. The apparatus of claim 1, wherein the controller is configured to:
provide a frequency signal corresponding to the biopotential measurement mode to the first chopper and the second chopper in response to the measurement mode being selected to be the impedance measurement mode and a carrier frequency for impedance measurement being within a band of noise caused by the amplifier.

6. The apparatus of claim 5, further comprising:
an analog-to-digital converter (ADC) configured to perform an analog-to-digital conversion on an output signal of the second chopper; and
a demodulator configured to demodulate the converted digital signal based on the carrier frequency.

7. The apparatus of claim 5, further comprising:
a third chopper configured to demodulate an output signal of the second chopper, using the carrier frequency.

8. The apparatus of claim 7, wherein the controller is configured to:
control the third chopper for the output signal of the second chopper to pass the third chopper undemodulated in response to the measurement mode being selected to be the biopotential measurement mode.

9. The apparatus of claim 1, wherein the controller comprises:
a first multiplexer (MUX) configured to selectively provide a first frequency signal or a constant voltage signal to the first chopper; and
a second MUX configured to selectively provide the first frequency signal or a second frequency signal to the second chopper.

10. The apparatus of claim 9, wherein the controller further comprises:
a phase shifter configured to shift a phase of the second frequency signal.

11. The apparatus of claim 9, further comprising:
a current generator configured to generate a current for impedance measurement based on the second frequency signal,
wherein the controller is configured to activate the current generator in response to the measurement mode being selected to be the impedance measurement mode.

12. The apparatus of claim 1, further comprising:
a resistance unit configured to implement a resistance component between a node for a bias voltage and a node between the first chopper and the amplifier, using a capacitor and at least two switches,
wherein the controller is configured to activate the resistance unit in response to the measurement mode being selected to be the biopotential measurement mode.

13. The apparatus of claim 1, further comprising:
a resistance unit configured to
implement a first resistance component between a node for a bias voltage and a first node between the first chopper and the amplifier, using at least two resistors, and
implement a second resistance component having a same resistance value as the first resistance component between the node for the bias voltage and a second node between the first chopper and the amplifier, using the at least two resistors,
wherein the controller is configured to activate the resistance unit in response to the measurement mode being selected to be the impedance measurement mode.

14. The apparatus of claim 1, further comprising:
a recovery unit configured to provide a voltage corresponding to a normal operation range of the amplifier to the amplifier.

15. A reconfigurable measuring apparatus comprising:
measuring modules, each of which is selectively configured to measure a biopotential and an impedance; and
a controller configured to control which of the biopotential and the impedance to measure by each of the measuring modules,
wherein each of the measuring modules comprises
a modulator configured to modulate an input signal,
an amplifier configured to amplify an output or internal signal of the modulator, and
a demodulator configured to demodulate an output signal of the amplifier, wherein, for each of the measuring modules, the controller is configured to control the modulator to modulate the input signal in response to the measuring module measuring the biopotential, and control the modulator to pass the input signal unmodulated in response to the measuring module measuring the impedance.

16. The apparatus of claim 15, wherein the controller is configured to:

selectively provide a frequency signal to the modulator and the demodulator included in each of the measuring modules selected to measure the biopotential.

17. The apparatus of claim 16, wherein the frequency signal has a frequency higher than a band of noise caused by the amplifier included in each of the measuring modules selected to measure the biopotential.

18. The apparatus of claim 15, wherein the controller is configured to:

provide a constant voltage signal to the modulator included in each of the measuring modules selected to measure the impedance; and provide a frequency signal to the demodulator included in each of the measuring modules selected to measure the impedance.

19. The apparatus of claim 18, wherein the frequency signal has a frequency identical to a carrier frequency for impedance measurement.

20. The apparatus of claim 15, wherein, in response to a carrier frequency for impedance measurement being within a band of noise caused by the amplifier included in each of the measuring modules selected to measure the impedance, the controller is configured to:

provide a frequency signal, having a frequency higher than the band of noise, to the modulator and the demodulator included in the measuring modules selected to measure the impedance.

21. A method of controlling a reconfigurable measuring apparatus, the method comprising:

receiving a signal indicating a measurement mode;

providing a first signal to a first chopper based on the measurement mode; and providing a second signal to a second chopper based on the measurement mode, wherein, in response to the measurement mode being a biopotential measurement mode, the first chopper is configured to modulate an input signal, using the first signal, and the second chopper is configured to demodulate the modulated input signal amplified by an amplifier, using the second signal, and wherein, in response to the measurement mode being an impedance measurement mode, the first chopper is configured to pass the input signal unmodulated and the second chopper is configured to demodulate the unmodulated input signal amplified by the amplifier, using the second signal.

22. The method of claim 21, wherein each of the first signal and the second signal comprises a frequency signal corresponding to the biopotential measurement mode in response to the measurement mode being the biopotential measurement mode.

23. The method of claim 21, wherein the first signal comprises a constant voltage signal in response to the measurement mode being the impedance measurement mode.

24. The method of claim 21, wherein the second signal comprises a frequency signal corresponding to the impedance measurement mode in response to the measurement mode being the impedance measurement mode.

25. The method of claim 21, wherein each of the first signal and the second signal comprises a frequency signal corresponding to the biopotential measurement mode in response to the measurement mode being the impedance measurement mode and a carrier frequency for impedance measurement being within a band of noise caused by the amplifier.

26. A non-transitory computer-readable storage medium storing a program comprising instructions to cause a computer to perform the method of claim 21.

27. A reconfigurable measuring apparatus comprising:

a first chopper configured to modulate a signal;

an amplifier configured to amplify the modulated signal;

a second chopper configured to demodulate the amplified signal; and a controller configured to control the first chopper and the second chopper based on whether a biopotential or an impedance of the signal is being measured, wherein the controller is configured to:

provide a first frequency signal of a first frequency to the first chopper and the second chopper in response to the biopotential being measured;

provide a constant voltage signal to the first chopper, and provide a second frequency signal of a second frequency greater than the first frequency to the second chopper, in response to the impedance being measured and the second frequency being outside a band of noise caused by the amplifier; and provide the first frequency signal to the first chopper and the second chopper in response to the impedance being measured and the second frequency being within the band of noise.

28. A reconfigurable measuring apparatus comprising:

a first chopper configured to modulate an input signal;

an amplifier configured to amplify an output signal of the first chopper;

a second chopper configured to demodulate an output or internal signal of the amplifier; and a controller configured to control the first chopper and the second chopper based on a measurement mode, wherein the controller controls the first chopper and the second chopper by:

providing a first frequency to the first chopper and the second chopper, in response to the measurement mode being a biopotential measurement mode, and providing a reference voltage to the first chopper to control the first chopper to pass the first signal unmodulated and providing a second frequency to the second chopper, in response to the measurement mode being an impedance measurement mode.

* * * * *